(12) United States Patent
Sullivan

(10) Patent No.: US 9,217,702 B2
(45) Date of Patent: *Dec. 22, 2015

(54) BIOMARKER NORMALIZATION

(75) Inventor: Benjamin Sullivan, San Diego, CA (US)

(73) Assignee: The Regents of the University of California, Oakland, CA (US)

(*) Notice: Subject to any disclaimer, the term of this patent is extended or adjusted under 35 U.S.C. 154(b) by 944 days.

This patent is subject to a terminal disclaimer.

(21) Appl. No.: 13/299,197

(22) Filed: Nov. 17, 2011

(65) Prior Publication Data

US 2012/0060590 A1    Mar. 15, 2012

Related U.S. Application Data

(63) Continuation of application No. 13/031,051, filed on Feb. 18, 2011, which is a continuation of application No. 12/104,355, filed on Apr. 16, 2008, now Pat. No. 7,905,134, which is a continuation-in-part of application No. 11/358,986, filed on Feb. 21, 2006, now Pat. No. 7,574,902, which is a continuation of application No. 10/400,617, filed on Mar. 25, 2003, now Pat. No. 7,017,394.

(60) Provisional application No. 60/401,432, filed on Aug. 6, 2002, provisional application No. 60/912,129, filed on Apr. 16, 2007.

(51) Int. Cl.
G01N 33/48 (2006.01)
G01N 13/04 (2006.01)
G01N 27/26 (2006.01)
G06F 19/24 (2011.01)

(52) U.S. Cl.
CPC ............... *G01N 13/04* (2013.01); *G01N 27/26* (2013.01); *G06F 19/24* (2013.01)

(58) Field of Classification Search
CPC ...................................................... G06F 19/24
USPC .......................................................... 702/19
See application file for complete search history.

(56) References Cited

U.S. PATENT DOCUMENTS

| | | | |
|---|---|---|---|
| 4,028,931 A | 6/1977 | Bisera | |
| 4,123,701 A | 10/1978 | Josefsen | |
| 4,150,564 A | 4/1979 | Barlow | |
| 4,245,495 A | 1/1981 | Kakiuchi | |
| 4,269,197 A | 5/1981 | Gilbard | |
| 4,305,823 A | 12/1981 | Batzer | |
| 4,436,094 A | 3/1984 | Cerami | |
| 4,455,864 A | 6/1984 | Wallner | |
| 4,475,556 A | 10/1984 | Reiff | |
| 4,587,003 A | 5/1986 | Tantram et al. | |
| 4,603,699 A | 8/1986 | Himpens | |
| 4,706,495 A | 11/1987 | Steudle | |
| 4,872,956 A | 10/1989 | Kotani et al. | |
| 4,951,683 A | 8/1990 | Davis | |
| 4,996,993 A | 3/1991 | York | |
| 5,005,403 A | 4/1991 | Steudle | |
| 5,143,080 A | 9/1992 | York | |
| 5,202,261 A | 4/1993 | Musho et al. | |
| 5,211,055 A | 5/1993 | Steudle | |
| 5,230,864 A | 7/1993 | Columbus | |
| 5,388,449 A | 2/1995 | LeVeen | |
| 5,489,515 A | 2/1996 | Hatschek et al. | |
| 5,591,636 A | 1/1997 | Grass | |
| 5,665,904 A | 9/1997 | Boling | |
| 5,766,435 A | 6/1998 | Liao | |
| 5,798,031 A | 8/1998 | Charlton et al. | |
| 5,810,725 A | 9/1998 | Sugihara | |
| 5,869,231 A | 2/1999 | Romisch | |
| 5,997,817 A | 12/1999 | Crismore et al. | |
| 6,214,208 B1 | 4/2001 | Ando et al. | |
| 6,224,550 B1 | 5/2001 | Ellingsen | |
| 6,695,964 B1 | 2/2004 | Ando et al. | |
| 6,894,511 B2 | 5/2005 | Yukimasa | |
| 7,017,394 B2 | 3/2006 | Sullivan | |
| 7,051,569 B2 | 5/2006 | Sullivan et al. | |
| 7,111,502 B2 | 9/2006 | Sullivan et al. | |
| 7,204,122 B2 | 4/2007 | Sullivan et al. | |
| 7,344,679 B2 | 3/2008 | Natarajan et al. | |
| 7,574,902 B2 | 8/2009 | Sullivan | |

(Continued)

FOREIGN PATENT DOCUMENTS

DE    3414866    10/1985
DE    3414866 A1    10/1985

(Continued)

OTHER PUBLICATIONS

Claudino et al., BIOSIS abstract #002246922, The role of cGMP on uroguanylin responses in salt-loaded rats, Annual Meeting of Professional Research Scientists on Experimental Biology, New Orleans, Louisiana, USA, Apr. 20-24, 2002; FASEB Journal 16:A956, Mar. 22, 2002.

(Continued)

*Primary Examiner* — Jerry Lin

(74) *Attorney, Agent, or Firm* — Fish & Richardson P.C.

(57) ABSTRACT

A fluid sample is measured with a tear film measuring system that includes a processing device that receives a sample chip comprising a sample region configured to contain an aliquot volume of sample fluid, the processing device configured to perform analyzes of osmolarity and of one or more biomarkers within the sample fluid, wherein the analysis of biomarkers includes normalization of biomarker concentration values.

39 Claims, 15 Drawing Sheets

(56) References Cited

U.S. PATENT DOCUMENTS

| | | |
|---|---|---|
| 7,905,134 B2 | 3/2011 | Sullivan |
| 7,987,702 B2 | 8/2011 | Sullivan |
| 8,020,433 B2 | 9/2011 | Sullivan et al. |
| 8,628,731 B2 | 1/2014 | Donsky et al. |
| 2002/0031813 A1 | 3/2002 | Ozkan |
| 2002/0049389 A1 | 4/2002 | Abreu |
| 2002/0094580 A1 | 7/2002 | Jorgensen |
| 2002/0182627 A1 | 12/2002 | Wang |
| 2003/0054342 A1 | 3/2003 | Star |
| 2003/0211625 A1 | 11/2003 | Cohan et al. |
| 2004/0036485 A1 | 2/2004 | Sullivan |
| 2005/0104606 A1 | 5/2005 | Donsky |
| 2005/0106714 A1 | 5/2005 | Zarur et al. |
| 2006/0107729 A1 | 5/2006 | Sullivan |
| 2006/0141469 A1 | 6/2006 | Rossier |
| 2007/0086927 A1 | 4/2007 | Natarajan |
| 2008/0050282 A1 | 2/2008 | Natarajan |
| 2008/0053206 A1 | 3/2008 | Natarajan |
| 2008/0057569 A1 | 3/2008 | Natarajan |
| 2008/0103376 A1 | 5/2008 | Felder |
| 2008/0273171 A1 | 11/2008 | Huth et al. |
| 2008/0286750 A1 | 11/2008 | Xu et al. |
| 2009/0221431 A1 | 9/2009 | Yoo |
| 2011/0144919 A1 | 6/2011 | Sullivan |
| 2013/0220833 A1 | 8/2013 | Sullivan |
| 2013/0233061 A1 | 9/2013 | Sullivan |

FOREIGN PATENT DOCUMENTS

| | | |
|---|---|---|
| EP | 0571066 A2 | 11/1993 |
| EP | 0467219 | 9/1998 |
| JP | S55-42048 | 3/1980 |
| JP | S63-148159 | 6/1988 |
| JP | H0353550 | 3/1991 |
| JP | H0961312 | 3/1997 |
| WO | 87/00286 A1 | 1/1987 |
| WO | WO 90/12314 | 10/1990 |
| WO | WO 93/22054 | 11/1993 |
| WO | WO 93/22058 | 11/1993 |
| WO | 96/14571 A1 | 5/1996 |
| WO | WO 97/36681 | 10/1997 |
| WO | WO 98/35225 | 8/1998 |
| WO | 99/23938 A1 | 5/1999 |
| WO | WO 00/62047 | 10/2000 |
| WO | WO 01/43875 | 6/2001 |
| WO | WO 01/53798 | 7/2001 |
| WO | WO 02/054067 | 7/2002 |
| WO | 02/103354 A1 | 12/2002 |
| WO | 2005/076796 A2 | 8/2005 |

OTHER PUBLICATIONS

Communication from the International Searching Authority re: Invitation to Pay Additional Fees and Annex re: Results of the Partial International Search for PCT/US03/09553, Oct. 20, 2003.

Farris, R.L., Tear osmolarity—a new gold standard, 1994, pp. 495-503.

Geerling et al., Quality of salivary tears following autologous submandibular gland transplantation for severe dry eye, Graefe's Arch. Clin. Exp. Opthalmol, 238:45-52, 2000, XP-002485949.

Gilbard, J.P. et al. Changes in tear ion concentrations in dry-eye disorders, May 2001, p. 529-533.

Chandler, D.E., et al., "Detection of calcium signals in neutrophils using fluorescent dyes," Luminescense Applications, 1989, No. 383, pp. 70-83.

Grodzinsky, A.J., "Fields, forces and flows in biological tissues and membranes," MIT Department of Electrical Engineering, 1995, pp. 191-197.

Lemp, M., "Report of the national eye institute/industry workshop on clinical trials in dry eyes," The CLAO Journal, vol. 21, No. 4, Oct. 1995, pp. 221-232.

Mitsubayashi, K., et al., "Flexible conductimetric sensor," Anal. Chem. 1993, 65, pp. 3586-3590.

Ogasawara et al., "Electrical conductivity of tear fluid in healthy persons and keratoconjunctivitis sicca patients measured by a flexible conductimetric sensor," Graefe's Arch. Clin. Exp. Opthlmao. 234:542-546 (1996).

Papageorgiou, G.C., et al., "A sensitive method for the estimation of the cytoplasmic osmolarity of cyanobacterial cells using chlorophyll a fluorescence," Biochimica et al. Biophusica Acta, 1997, vol. 1335, No. 1/2, pp. 1-4.

Pensyl, C.D. et al., "Vapor pressure osmometry: minimum sample microvolumes," Acta Opthalmol Scan 77 (1), Feb. 1999, pp. 27-30.

Schaumberg, "Aging and sex-steroid hormone influences in dry eye syndrome," ARVO Abstract from IOVS, Mar. 15, 2001, vol. 42, No. 4.

Extended European Search Report in EP Application No. E 12187075.2-1553, dated Apr. 3, 2013, 7 pages.

Extended European Search Report in EP Application No. 10184812.5-1553, dated Apr. 16, 2014, 8 pages.

International Search Report and Written Opinion in International Application No. PCT/US2008/060526, mailed Jul. 10, 2008, 10 pages.

International Preliminary Report on Patentability in International Application No. PCT/US2008/060526, issued Oct. 20, 2009, 8 pages.

Nishihara et al., "Method for Measuring Concentration of Drug in Tear Fluid," Examination & Technique, 1990, 18(6):892-893.

BIOMARKER NORMALIZATION

CROSS-REFERENCES TO RELATED APPLICATIONS

This application is a continuation of U.S. Non-Provisional application Ser. No. 13/031,051 entitled "Biomarker Normalization" filed Feb. 18, 2011, which is a continuation of U.S. Non-Provisional application Ser. No. 12/104,355 entitled "Biomarker Normalization" filed Apr. 16, 2008 (now U.S. Pat. No. 7,905,134), which is a continuation-in-part of U.S. Non-Provisional application Ser. No. 11/358,986 entitled "Tear Film Osmometry" filed on Feb. 21, 2006 (now U.S. Pat. No. 7,574,902), which is a continuation application of U.S. Non-Provisional application Ser. No. 10/400,617 entitled "Tear Film Osmometry" filed Mar. 25, 2003 (now U.S. Pat. No. 7,017,394), which claims priority to U.S. Provisional Patent Application Ser. No. 60/401,432 entitled "Volume Independent Tear Film Osmometer" filed Aug. 6, 2002. Said U.S. Non-Provisional application Ser. No. 12/104,355 also claims the benefit of priority under 35 U.S.C. §119 to U.S. Provisional Application Ser. No. 60/912,129 entitled "Biomarker Normalization" filed on Apr. 16, 2007. Each of these applications is incorporated herein in its entirety as if set forth in full.

BACKGROUND

1. Field of the Invention

The field of the invention relates generally to osmolarity measurements and more particularly to systems and methods for calibrating tear film osmolarity measuring devices.

2. Background Information

Tears fulfill an essential role in maintaining ocular surface integrity, protecting against microbial challenge, and preserving visual acuity. These functions, in turn, are critically dependent upon the composition and stability of the tear film structure, which includes an underlying mucin foundation, a middle aqueous component, and an overlying lipid layer. Disruption, deficiency, or absence of the tear film can severely impact the eye. If unmanaged with artificial tear substitutes or tear film conservation therapy, these disorders can lead to intractable desiccation of the corneal epithelium, ulceration and perforation of the cornea, an increased incidence of infectious disease, and ultimately pronounced visual impairment and blindness.

Keratoconjunctivitis sicca (KCS), or "dry eye", is a condition in which one or more of the tear film structure components listed above is present in insufficient volume or is otherwise out of balance with the other components. It is known that the (fluid tonicity or osmolarity of tears increases in patients with KCS. KCS is associated with conditions that affect the general health of the body, such as Sjogren's syndrome, aging, and androgen deficiency. Therefore, osmolarity of a tear film can be a sensitive and specific indicator for the diagnosis of KCS and other conditions.

The osmolarity of a sample fluid (e.g., a tear) can be determined by an ex vivo technique called "freezing point depression," in which solutes or ions in a solvent (i.e. water), cause a lowering of the fluid freezing point from what it would be without the ions. In the freezing point depression analysis the freezing point of the ionized sample fluid is found by detecting the temperature at which a quantity of the sample (typically on the order of about several milliliters) first begins to freeze in a container (e.g., a tube). To measure the freezing point, a volume of the sample fluid is collected into a container, such as a tube. Next, a temperature probe is immersed in the sample fluid, and the container is brought into contact with a freezing bath or Peltier cooling device. The sample is continuously stirred so as to achieve a supercooled liquid state below its freezing point. Upon mechanical induction, the sample solidifies, rising to its freezing point due to the thermodynamic heat of fusion. The deviation from the sample freezing point from 0° C. is proportional to the solute level in the sample fluid. This type of measuring device is sometimes referred to as an osmometer.

Presently, freezing point depression measurements are made ex vivo by removing tear samples from the eye using a micropipette or capillary tube and measuring the depression of the freezing point that results from heightened osmolarity. However, these ex vivo measurements are often plagued by many difficulties. For example, to perform freezing point depression analysis of the tear sample, a relatively large volume must be collected, typically on the order of 20 microliters (μL) of a tear film. Because no more than about 10 to 100 nanoliters (nL) of tear sample can be obtained at any one time from a KCS patient, the collection of sufficient amounts of fluid for conventional ex vivo techniques requires a physician to induce reflex tearing in the patient. Reflex tearing is caused by a sharp or prolonged irritation to the ocular surface, akin to when a large piece of dirt becomes lodged in one's eye. Reflex tears are more dilute, i.e. have fewer solute ions than the tears that are normally found on the eye. Any dilution of the tear film invalidates the diagnostic ability of an osmolarity test for dry eye, and therefore make currently available ex vivo methods prohibitive in a clinical setting.

A similar ex vivo technique is vapor pressure osmometry, where a small, circular piece of filter paper is lodged underneath a patient's eyelid until sufficient fluid is absorbed. The filter paper disc is placed into a sealed chamber, whereupon a cooled temperature sensor measures the condensation of vapor on its surface. Eventually the temperature sensor is raised to the dew point of the sample. The reduction in dew point proportional to water is then converted into osmolarity. Because of the induction of reflex tearing and the large volume requirements for existing vapor pressure osmometers, they are currently impractical for determination of dry eye.

The Clifton Nanoliter Osmometer (available from Clifton Technical Physics of Hartford, N.Y., USA) has been used extensively in laboratory settings to quantify the solute concentrations of KCS patients, but the machine requires a significant amount of training to operate. It generally requires hour-long calibrations and a skilled technician in order to generate acceptable data. The Clifton Nanoliter Osmometer is also bulky and relatively expensive. These characteristics seriously detract from it use as a clinical osmometer.

In contrast to ex vivo techniques that measure osmolarity of tear samples removed from the ocular surface, an in vivo technique that attempted to measure osmolarity directly on the ocular surface used a pair flexible pair of electrodes that were placed directly underneath the eyelid of the patient. The electrodes were then plugged into an LCR meter to determine the conductivity of the fluid surrounding them. While it has long been known that conductivity is directly related to the ionic concentration, and hence osmolarity of solutions, placing the sensor under the eyelid for half a minute likely induced reflex tearing. Furthermore, these electrodes were difficult to manufacture and posed increased health risks to the patient as compared to simply collecting tears with a capillary.

It should be apparent from the discussion above that current osmolarity measurement techniques are unavailable in a clinical setting and can't attain the volumes necessary for dry eye patients. Thus, there is a need for an improved, clinically feasible, nanoliter-scale osmolarity measurement. The present invention satisfies this need. Tears fulfill an essential role in maintaining ocular surface integrity, protecting against microbial challenge, and preserving visual acuity. These functions in turn, are critically dependent upon the composition and stability of the tear film structure, which includes an underlying mucin foundation, a middle aqueous component, and an overlying lipid layer. Disruption, deficiency, or absence of the tear film can severely impact the eye.

SUMMARY

In accordance with the invention, a fluid sample is measured with a tear film measuring system that includes a processing device that receives a sample chip comprising a sample region configured to contain an aliquot volume of sample fluid, the processing device configured to perform analyses of osmolarity and of one or more biomarkers within the sample fluid, wherein the analysis of biomarkers includes normalization of biomarker concentration values. Processing in accordance with the invention includes receiving an output signal from a sample region of a sample chip that is configured to produce an osmolarity output signal that indicates energy properties of an aliquot volume of the sample fluid, wherein the osmolarity output signal is correlated with osmolarity of the sample fluid, receiving an output signal from the sample region of the sample chip that is configured to produce a biomarker output signal that indicates chemical properties of the sample fluid, wherein the biomarker output signal is correlated with biomarker concentration of the sample fluid, processing the osmolarity output signal to produce an osmolarity value for the sample fluid and processing the biomarker output signal to produce a biomarker concentration value for the sample fluid, and determining an Adjusted Biomarker Level that provides normalization of biomarker concentration values. The normalization of biomarker concentration values can correct for patient-specific tear homeostasis and for clinician induced tear sampling variance in connection with obtaining the sample fluid. The processing of the osmolarity output signal and processing the biomarker output signal can be performed simultaneously or serially.

These and other features, aspects, and embodiments of the invention are described below in the section entitled "Detailed Description."

BRIEF DESCRIPTION OF THE DRAWINGS

Features, aspects, and embodiments of the inventions are described in conjunction with the attached drawings, in which.

DETAILED DESCRIPTION

Exemplary embodiments are described for measuring the osmolarity of an aliquot volume of a sample fluid (e.g., tear film, sweat, blood, or other fluids). The exemplary embodiments are configured to be relatively fast, non-invasive, inexpensive, and easy to use, with minimal injury of risk to the patient. Accurate measurements can be provided with as little as nanoliter volumes of a sample fluid. For example, a measuring device configured in accordance with the invention enables osmolarity measurement with no more than 200 µL of sample fluid, and typically much smaller volumes can be successfully measured. In one embodiment described further below, osmolarity measurement accuracy is not compromised by variations in the volume of sample fluid collected, so that osmolarity measurement is substantially independent of collected volume. The sample fluid can include tear film, sweat, blood, or other bodily fluids. It should be noted, however, that sample fluid can comprise other fluids, such as milk or other beverages.

Figure 1:
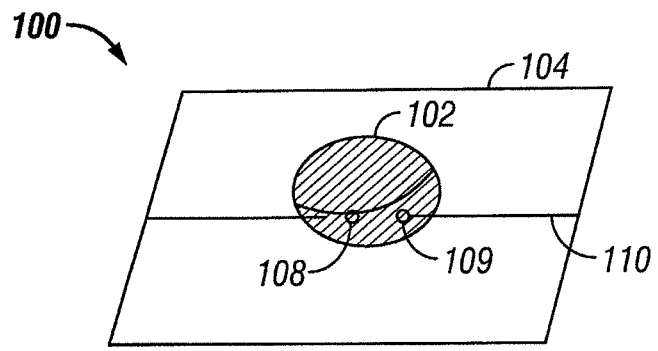
FIG. 1 illustrates an aliquot-sized sample receiving chip for measuring the osmolarity of a sample fluid.

FIG. 1 illustrates an exemplary embodiment of an osmolarity chip 100 that can be used to measure the osmolarity of a sample fluid 102, such as a tear film sample. In the FIG. 1 embodiment, the chip 100 includes a substrate 104 with a sample region having sensor electrodes 108, 109 and circuit connections 110 imprinted on the substrate. The electrodes and circuit connections are preferably printed using well-known photolithographic techniques. For example, current techniques enable the electrodes 108, 109 to have a diameter in the range of approximately one (1) to eighty (80) microns, and spaced apart sufficiently so that no conductive path exists in the absence of sample fluid. Currently available techniques, however, can provide electrodes of less than one micron in diameter, and these are sufficient for a chip constructed in accordance with the invention. The amount of sample fluid needed for measurement is no more than is necessary to extend from one electrode to the other, thereby providing an operative conductive path. The photolithographic scale of the chip 100 permits the measurement to be made for aliquot-sized samples in a micro- or nano-scale level. For example, reliable osmolarity measurement can be obtained with a sample volume of less than 20 μL of tear film. A typical sample volume is less than one hundred nanoliters (100 nL). It is expected that it will be relatively easy to collect 10 nL of a tear film sample even from patients suffering from dry eye.

The chip 100 is configured to transfer energy to the sample fluid 102 and enable detection of the sample fluid energy properties. In this regard, a current source is applied across the electrodes 108, 109 through the connections 110. The osmolarity of the sample fluid can be measured by sensing the energy transfer properties of the sample fluid 102. The energy transfer properties can include, for example, electrical conductivity, such that the impedance of the sample fluid is measured, given a particular amount of electrical power (e.g., current) that is transferred into the sample through the connections 110 and the electrodes 108, 109.

If conductivity of the sample fluid is to be measured, then preferably a sinusoidal signal on the order of ten volts at approximately 100 kHz is applied. The real and imaginary parts of the complex impedance of the circuit path from one electrode 108 through the sample fluid 102 to the other electrode 109 are measured. At the frequencies of interest, it is likely that the majority of the electrical signal will be in the real half of the complex plane, which reduces to the conductivity of the sample fluid. This electrical signal (hereafter referred to as conductivity) can be directly related to the ion concentration of the sample fluid 102, and the osmolarity can be determined. Moreover, if the ion concentration of the sample fluid 102 changes, the electrical conductivity and the osmolarity of the fluid will change in a corresponding manner. Therefore, the osmolarity is reliably obtained. In addition, because the impedance value does not depend on the volume of the sample fluid 102, the osmolarity measurement can be made substantially independent of the sample volume.

As an alternative to the input signal described above, more complex signals can be applied to the sample fluid whose response will contribute to a more thorough estimate of osmolarity. For example, calibration can be achieved by measuring impedances over a range of frequencies. These impedances can be either simultaneously (via combined waveform input and Fourier decomposition) or sequentially measured. The frequency versus impedance data will provide information about the sample and the relative performance of the sample fluid measurement circuit.

Figure 2:
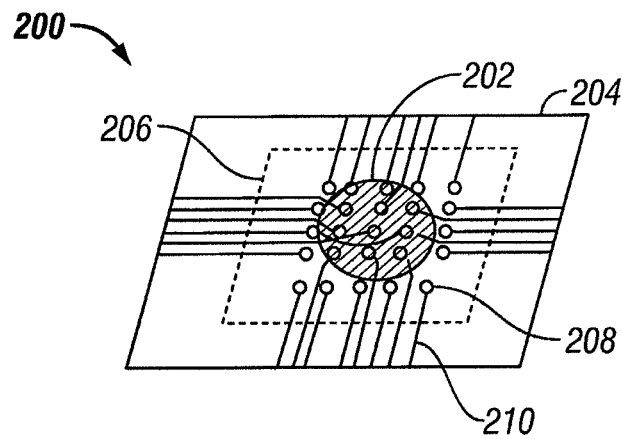
FIG. 2 illustrates an alternative embodiment of a sample receiving chip that includes a circuit region. with an array of electrodes imprinted with photolithography techniques.

FIG. 2 illustrates an alternative embodiment of a sample receiving chip 200 that measures osmolarity of a sample fluid 202, wherein the chip comprises a substrate layer 204 with a sample region 206 comprising an imprinted circuit that includes an array of electrodes 208. In the illustrated embodiment of FIG. 2, the sample region 206 has a 5-by-5 array of electrodes that are imprinted with photolithographic techniques, with each electrode 208 having a connection 210 to one side of the substrate 204. Not all of the electrodes 208 in FIG. 2 are shown with a connection, for simplicity of illustration. The electrodes provide measurements to a separate processing unit, described further below.

The electrode array of FIG. 2 provides a means to measure the size of the tear droplet 202 by detecting the extent of conducting electrodes 208 to thereby determine the extent of the droplet. In particular, processing circuitry can determine the number of electrodes that are conducting, and therefore the number of adjacent electrodes that are covered by the droplet 202 will be determined. The planar area of the substrate that is covered by the sample fluid is thereby determined. With a known nominal surface tension of the sample fluid, the height of the sample fluid volume over the planar area can be reliably estimated, and therefore the volume of the droplet 202 can be determined.

Figure 3:
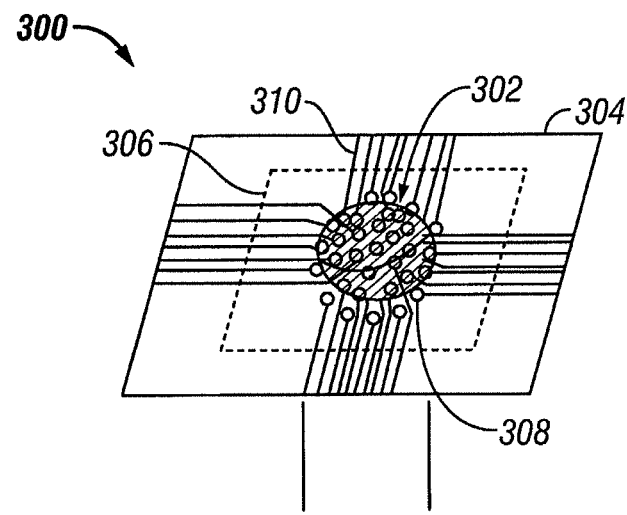
FIG. 3 illustrates another alternative embodiment of the FIG. 1 chip, wherein a circuit region includes printed electrodes arranged in a plurality of concentric circles.

FIG. 3 illustrates another alternative embodiment of a sample receiving chip 300 on which a sample fluid 302 is deposited. The chip comprises a substrate layer 304, wherein a sample region 306 is provided with electrodes 308 that are configured in a plurality of concentric circles. Each electrode 308 can be connected to one side of substrate layer 304 by connections 310. In a manner similar to the square array of FIG. 2, the circular arrangement of the FIG. 3 electrodes 308 also provides an estimate of the size of the sample fluid volume 302 because the droplet typically covers a circular or oval area of the sample region 302. Processing circuitry can detect the largest (outermost) circle of electrodes that are conducting, and thereby determine a planar area of coverage by the fluid sample. As before, the determined planar area provides a volume estimate, in conjunction with a known surface tension and corresponding volume height of the sample fluid 302. In the FIG. 3 illustrated embodiment, the electrodes 308 can be printed using well known photolithography techniques that currently permit electrodes to have a diameter in the range of one (1) to eighty (80) microns. This allows the submicroliter droplet to substantially cover the electrodes. The electrodes can be printed over an area sized to receive the sample fluid, generally covering 1 mm$^2$ to 1 cm$^2$.

The electrodes and connections shown in FIG. 1, FIG. 2, and FIG. 3 can be imprinted on the respective substrate layers as electrodes with contact pads, using photolithographic techniques. For example, the electrodes can be formed with different conductive metalization such as aluminum, platinum, titanium, titanium-tungsten, and other similar material. In one embodiment, the electrodes can be formed with a dielectric rim to protect field densities at the edges of the electrodes. This can reduce an otherwise unstable electric field at the rim of the electrode.

Figure 4:
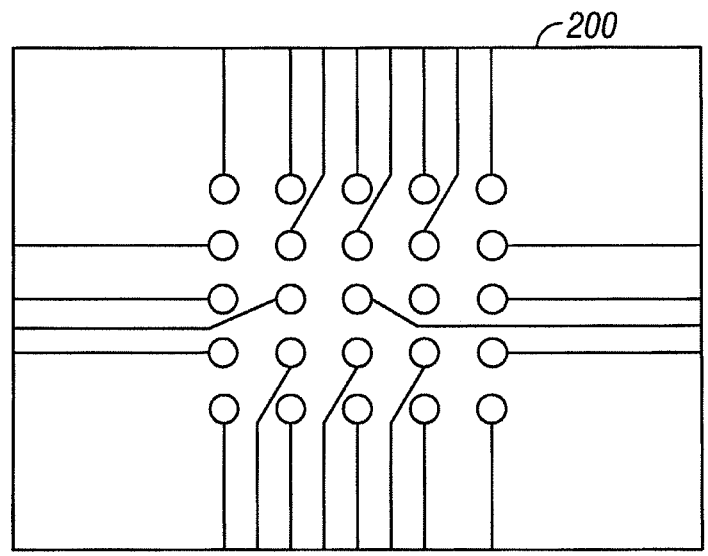
FIG. 4 is a top view of the chip shown in FIG. 2.
Figure 5:
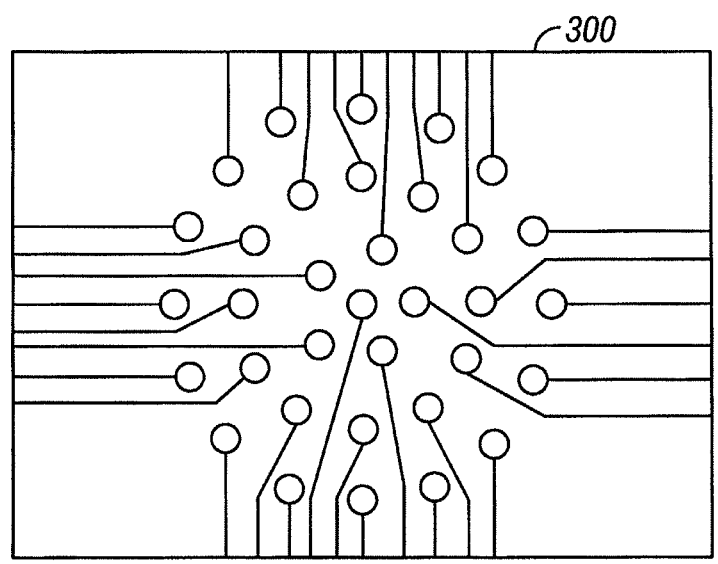
FIG. 5 is a top view of the chip shown in FIG. 3.

Top views of the exemplary embodiments of the chips 200 and 300 are illustrated in FIG. 4 and FIG. 5, respectively. The embodiments show the detailed layout of the electrodes and the connections, and illustrate how each electrode can be electrically connected for measuring the electrical properties of a sample droplet. As mentioned above, the layout of the electrodes and the connections can be imprinted on the substrate 100, 200, 300 using well-known photolithographic techniques.

Figure 6:
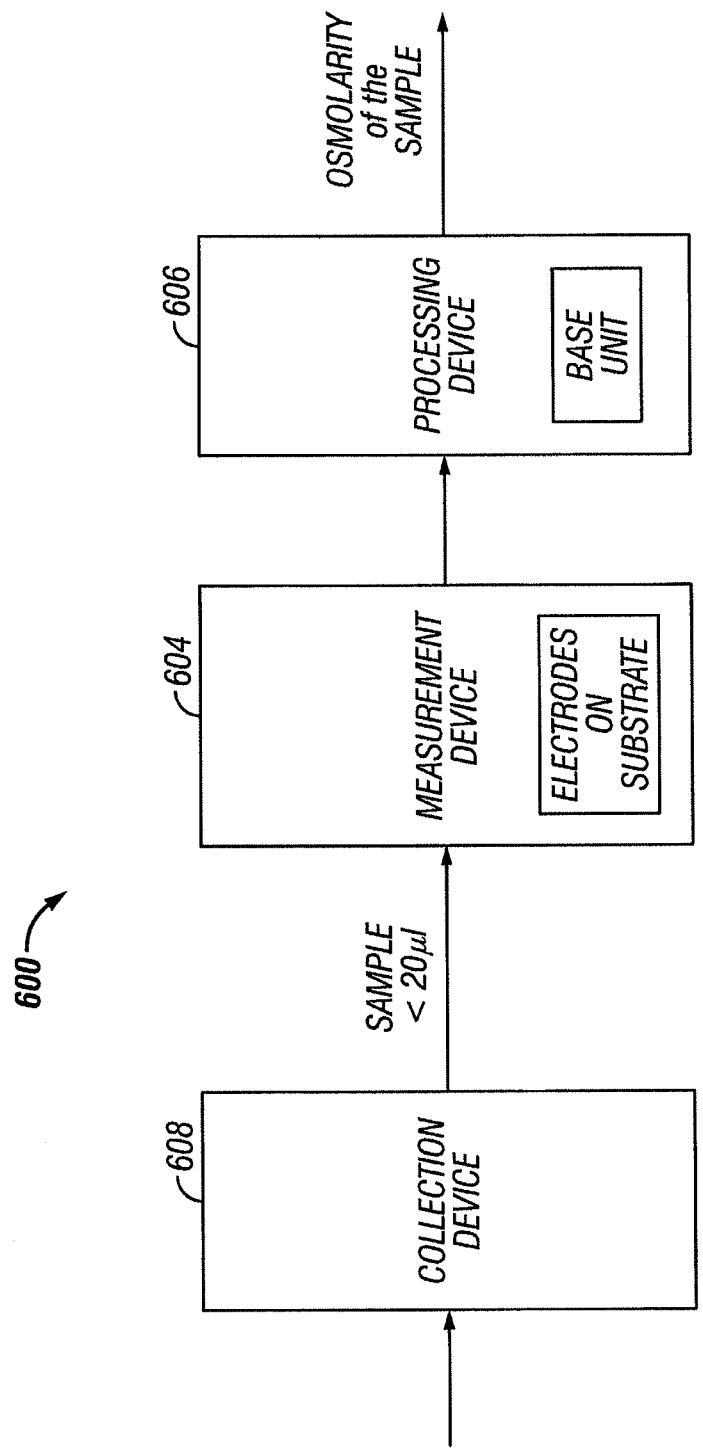
FIG. 6 is a block diagram of an osmolarity measurement system configured in accordance with the present invention.

FIG. 6 is a block diagram of an osmometry system 600 configured in accordance with an embodiment of the present invention, showing how information is determined and used in a process that determines osmolarity of a sample fluid. The osmometry system 600 includes a measurement device 604 and a processing device 606. The measurement device receives a volume of sample fluid from a collection device 608. The collection device can comprise, for example, a micropipette or capillary tube. The collection device 608 collects a sample tear film of a patient, such as by using negative pressure from a fixed-volume micropipette or charge attraction from a capillary tube to draw a small tear volume from the vicinity of the ocular surface of a patient.

The measurement device 604 can comprise a system that transfers energy to the fluid in the sample region and detects the imparted energy. For example, the measurement device

604 can comprise circuitry that provides electrical energy in a specified waveform (such as from a function generator) to the electrical path comprising two electrodes bridged by the sample fluid. The processing device 606 detects the energy imparted to the sample fluid and determines osmolarity. The processing device can comprise, for example, a system including an RLC multimeter that produces data relating to the reactance of the fluid that forms the conductive path between two electrodes, and including a processor that determines osmolarity through a table look-up scheme. If desired, the processing device can be housed in a base unit that receives one of the chips described above.

As mentioned above, a sample sufficient to provide an osmolarity measurement can contain less than 20 microliters (µL) of fluid. A typical sample of tear film in accordance with the invention is collected by a fluid collector such as a capillary tube, which often contains less than one microliter of tear film. Medical professionals will be familiar with the use of micropipettes and capillary tubes, and will be able to easily collect the small sample volumes described herein, even in the case of dry eye sufferers.

The collected sample fluid is expelled from the collection device 608 to the measurement device 604. The collection device can be positioned above the sample region of the chip substrate either manually by a medical professional or by being mechanically guided over the sample region. In one embodiment, for example, the collection device (e.g., a capillary tube) is mechanically guided into position with an injection-molded plastic hole in a base unit, or is fitted to a set of clamps with precision screws (e.g., a micromanipulator with needles for microchip interfaces). In another embodiment, the guide is a computer-guided feedback control circuitry that holds the capillary tube and automatically lowers it into the proper position.

The electrodes and connections of the chips measure energy properties of the sample fluid, such as conductivity, and enable the measured properties to received by the processing device 606. The measured energy properties of the sample fluid include electrical conductivity and can also include other parameters, such as both parts of the complex impedance of the sample, the variance of the noise in the output signal, and the measurement drift due to resistive heating of the sample fluid. The measured energy properties are processed in the processing device 606 to provide the osmolarity of the sample. In one embodiment, the processing device 606 comprises a base unit that can accept a chip and can provide electrical connection between the chip and the processing device 606. In another embodiment, the base unit can include a display unit for displaying osmolarity values. It should be noted that the processing device 606 and, in particular, the base unit can be a hand-held unit.

Figure 7:
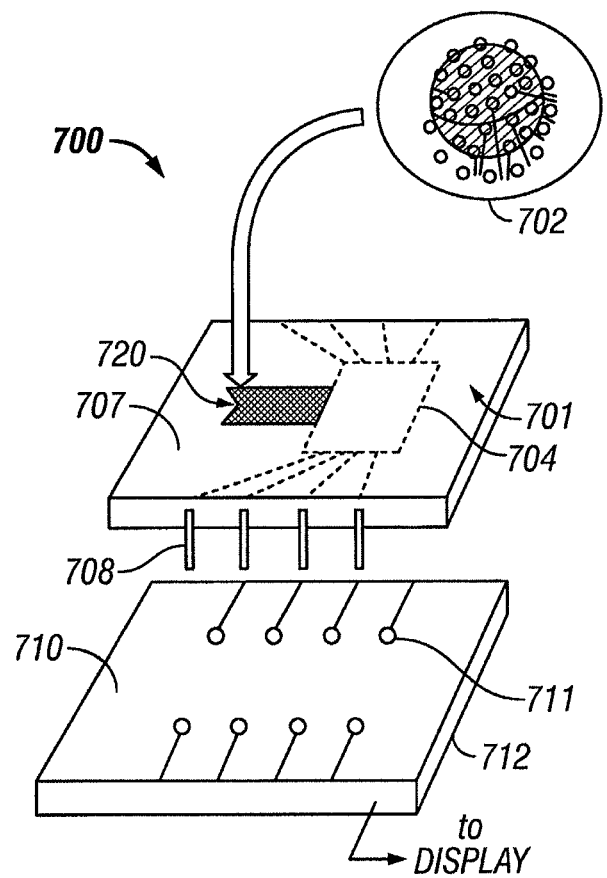
FIG. 7 is a perspective view of a tear film osmolarity measurement system constructed in accordance with the present invention.

FIG. 7 is a perspective view of a tear film osmolarity measuring system 700 constructed in accordance with the present invention. In the illustrated embodiment of FIG. 7, the exemplary system 700 includes a measuring unit 701 that comprises a chip, such as one of the chips described above, and a connector or socket base 710, which provides the appropriate measurement output. The system 700 determines osmolarity by measuring electrical conductivity of the sample fluid: Therefore, the measurement chip 701 comprises a semiconductor integrated circuit (IC) chip with a substrate having a construction similar to that of the chips described above in connection with FIG. 1 through FIG. 5. Thus, the chip 701 includes a substrate layer with a sample region that is defined by at least two electrodes printed onto the substrate layer (such details are of a scale too small to be visible in FIG. 7; see FIG. 1 through FIG. 5). The substrate and sample region are encased within an inert package, in a manner that will be known to those skilled in the art. In particular, the chip 701 is fabricated using conventional semiconductor fabrication techniques into an IC package 707 that includes electrical connection legs 708 that permit electrical signals to be received by the chip 701 and output to be communicated outside of the chip. The packaging 707 provides a casing that makes handling of the chip more convenient and helps reduce evaporation of the sample fluid.

Figure 8:
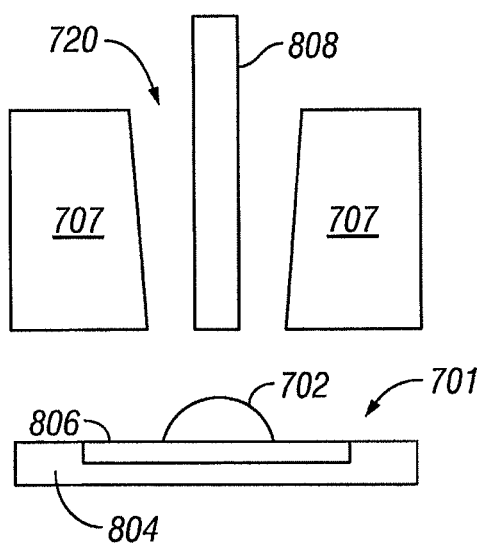
FIG. 8 is a side section of the sample receiving chip showing the opening in the exterior packaging.

FIG. 8 shows that the measurement chip 701 is fabricated with an exterior opening hole 720 into which the sample fluid 702 is inserted. Thus, the hole 720 can be formed in the semiconductor packaging 707 to provide a path through the chip exterior to the substrate 804 and the sample region 806. The collection device (such as a micropipette or capillary tube) 808 is positioned into the hole 720 such that the sample fluid 702 is expelled from the collection device directly onto the sample region 806 of the substrate 804. The hole 720 is sized to receive the tip of the collection device. The hole 720 forms an opening or funnel that leads from the exterior of the chip onto the sample region 806 of the substrate 804. In this way, the sample fluid 702 is expelled from the collection device 808 and is deposited directly on the sample region 806 of the substrate 804. The sample region is sized to receive the volume of sample fluid from the collection device. In FIG. 8, for example, the electrodes form a sample region 806 that is generally in a range of approximately 1 $mm^2$ to 1 $cm^2$ in area.

Returning to FIG. 7, the chip 701 can include processing circuitry 704 that comprises, for example, a function generator that generates a signal of a desired waveform, which is applied to the sample region electrodes of the chip, and a voltage measuring device to measure the root-mean-square (RMS) voltage value that is read from the chip electrodes. The function generator can produce high frequency alternating current (AC) to avoid undesirable direct current (DC) effects for the measurement process. The voltage measuring device can incorporate the functionality of an RLC measuring device. Thus, the chip 701 can incorporate the measurement circuitry as well as the sample region electrodes. The processing circuitry can include a central processing unit (CPU) and associated memory that can store programming instructions (such as firmware) and also can store data. In this way, a single chip can include the electrodes and associated connections for the sample region, and on a separate region of the chip, can also include the measurement circuitry. This configuration will minimize the associated stray resistances of the circuit structures.

As noted above, the processing circuitry 70 applies a signal waveform to the sample region electrodes. The processing circuitry also receives the energy property signals from the electrodes and determines the osmolarity value of the sample fluid. For example, the processing unit receives electrical conductivity values from a set of electrode pairs. Those skilled in the art will be familiar with techniques and circuitry for determining the conductivity of a sample fluid that forms a conducting path between two or more electrodes.

Figure 9:
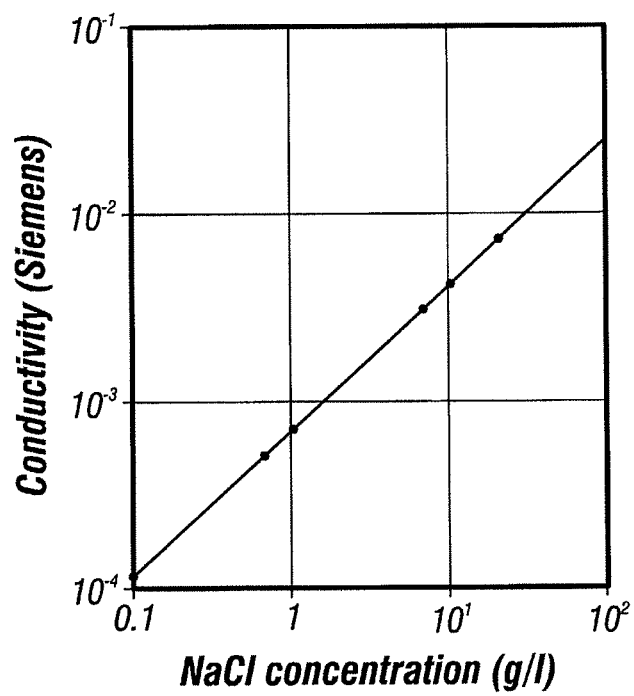
FIG. 9 is a calibration curve relating the sodium content of the sample fluid with electrical conductivity.

In the FIG. 7 embodiment, the processing unit 704 produces signal waveforms at a single frequency, such as 100 kHz and 10 Volts peak-to-peak. The processing circuitry 704 then determines the osmolarity value from the sodium content correlated to the electrical conductivity using a calibration curve, such as the curve shown in FIG. 9. In this case, the calibration curve is constructed as a transfer function between the electrical conductivity (voltage) and the osmolarity value (i.e., the sodium content). It should be noted, however, that other calibration curves can also be constructed to provide transfer functions between other energy properties and the osmolarity value. For example, the variance, autocorrelation and drift of the signal can be included in an osmolarity calculation. If desired, the osmolarity value can also be built upon multi-variable correlation coefficient charts or neural network interpretation so that the osmolarity value can be optimized with an arbitrarily large set of measured variables.

In an alternate form of the FIG. 7 embodiment, the processing unit 704 produces signal waveforms of a predetermined frequency sweep, such as 1 kHz to 100 kHz in 1 kHz increments, and stores the conductivity and variance values received from the set of electrode pairs at each frequency. The output signal versus frequency curve can then be used to provide higher order information about the sample which can be used with the aforementioned transfer functions to produce an ideal osmolarity reading.

As shown in FIG. 7, the base socket connector 710 receives the pins 708 of the chip 701 into corresponding sockets 711. The connector 710, for example, can supply the requisite electrical power to the processing circuitry 704 and electrodes of the chip. Thus, the chip 701 can include the sample region electrodes and the signal generator and processing circuitry necessary for determining osmolarity, and the output comprising the osmolarity value can be communicated off the chip via the pins 708 through the connector 710 and to a display readout.

If desired, the base connector socket 710 can include a Peltier layer 712 located beneath the sockets that receive the pins 708 of the chip 701. Those skilled in the art will understand that a Peltier layer comprises an electrical/ceramic junction such that properly applied current can cool or heat the Peltier layer. In this way, the sample chip 701 can be heated or cooled, thereby further controlling evaporation of the sample fluid. It should be apparent that evaporation of the sample fluid should be carefully controlled, to ensure accurate osmolarity values obtained from the sample fluid.

Figure 10:
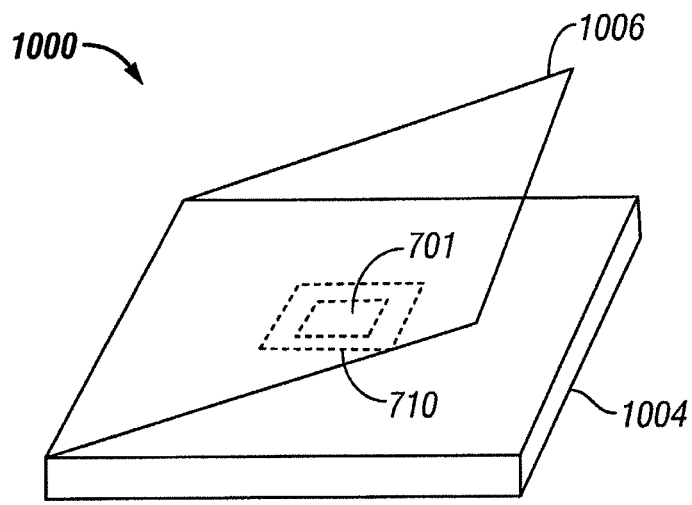
FIG. 10 illustrates a hinged base unit of the osmometer that utilizes the sample receiving chips described in FIGS. 1-5.

FIG. 10 shows an alternative embodiment of an osmometer in which the chip does not include an on-chip processing unit such as described above, but rather includes limited circuitry comprising primarily the sample region electrodes and interconnections. That is, the processing unit is separately located from the chip and can be provided in the base unit.

FIG. 10 shows in detail an osmometer 1000 that includes a base unit 1004, which houses the base connector 710, and a hinged cover 1006 that closes over the base connector 710 and a received measurement chip 701. Thus, after the sample fluid has been dispensed on the chip, the chip is inserted into the socket connector 710 of the base unit 1004 and the hinged cover 1006 is closed over the chip to reduce the rate of evaporation of the sample fluid.

It should be noted that the problem with relatively fast evaporation of the sample fluid can generally be handled in one of two ways. One way is to measure the sample fluid voltage quickly as soon possible after the droplet is placed on the sample region of the chip. Another way is to enable the measuring unit to measure the rate of evaporation along with the corresponding changes in conductivity values. The processing unit can then post-process the output to estimate the osmolarity value. The processing can be performed in the hardware or in software stored in the hardware. Thus, the processing unit can incorporate different processing techniques such as using neural networks to collect and learn about characteristics of the fluid samples being measured for osmolarity, as well as temperature variations, volume changes, and other related parameters so that the system can be trained in accordance with neural network techniques to make faster and more accurate osmolarity measurements.

Figure 11:
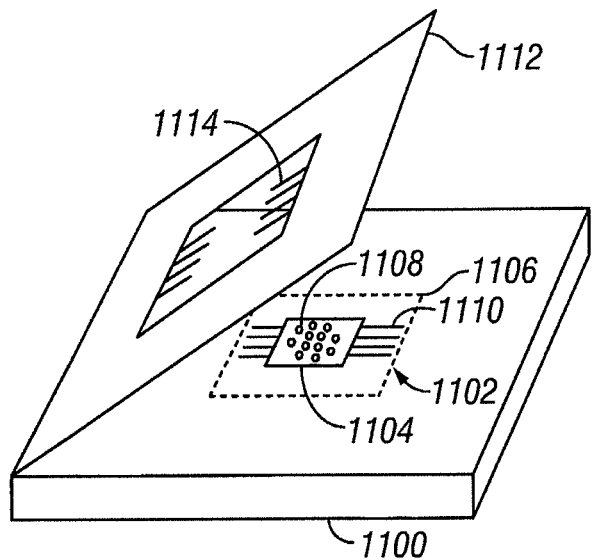
FIG. 11 illustrates a probe card configuration for the sample receiving chip and processing unit.

FIG. 11 shows another alternative construction, in which the osmolarity system utilizes a sample receiving chip 1102 that does not include IC packaging such as shown in FIG. 7. Rather, the FIG. 11 measurement chip 1102 is configured as a chip with an exposed sample region comprising the electrodes and associated connections, but the processing circuitry is located in the base unit for measuring the energy properties of the sample fluid. In this alternative construction, a connector similar to the connector socket 710 allows transmission of measured energy properties to the processing unit in the base unit. Those skilled in the art will understand that such a configuration is commonly referred to a probe card structure.

FIG. 11 shows a probe card base unit 1100 that receives a sample chip probe card 1102 that comprises a substrate 1104 with a sample region 1106 on which are formed electrodes 1108 that are wire bonded to edge connectors 1110 of the probe card. When the hinged lid 1112 of the base unit is closed down over the probe card, connecting tines 1114 on the underside of the lid come into mating contact with the edge connectors 1110. In this way, the electrodes of the sample region 1106 are coupled to the processing circuitry and measurement can take place. The processing circuitry of the probe card embodiment of FIG. 11 can be configured in either of the configurations described above. That is, the processing to apply current to the electrodes and to detect energy properties of the sample fluid and determine osmolarity can be located on-chip, on the substrate of the probe card 1102, or the processing circuitry can be located off-chip, in the base unit 1100.

In all the alternative embodiments described above, the osmometer is used by placing a new measurement chip into the base unit while the hinged top is open. Upon placement into the base unit the chip is lowered up and begins monitoring its environment. Recording output signals from the chip at a rate of, for example, 1 kHz, will fully capture the behavior of the system. Placing a sample onto any portion of the electrode array generates high signal-to-noise increase in conductivity between ally pair of electrodes covered by the sample fluid. The processing unit will recognize the change in conductivity as being directly related to the addition of sample fluid, and will begin conversion of electronic signals into osmolarity data once this type of change is identified. This strategy occurs without intervention by medical professionals. That is, the chip processing is initiated upon coupling to the base unit and is not dependent on operating the lid of the base unit or any other user intervention.

In any of the configurations described above, either the "smart chip" with processing circuitry on-chip (FIG. 7), or the electrode-only configuration with processing circuitry off-chip (FIG. 10), in a packaged chip (FIG. 7 and FIG. 10) or in a probe card (FIG. 11), the sample receiving chip can be disposed of after each use, so that the base unit serves as a platform for interfacing with the disposable measurement chip. As noted, the base unit can also include relevant control, communication, and display circuits (not shown), as well as software, or such features can be provided off-chip in the base unit. In this regard, the processing circuitry can be configured to automatically provide sufficient power to the sample region electrodes to irreversibly oxidize them after a measurement cycle, such that the electrodes are rendered inoperable for any subsequent measurement cycle. Upon inserted a used chip into the base unit, the user will be given an indication that the electrodes are inoperable. This helps prevent inadvertent multiple use of a sample chip, which can lead to inaccurate osmolarity readings and potentially unsanitary conditions.

A secondary approach to ensure that a previously used chip is not placed back into the machine includes encoding serial numbers, or codes directly onto the chip. The base unit will store the used chip numbers in memory and cross-reference them against new chips placed in the base connector. If the base unit finds that the serial number of the used chip is the same as an old chip, then the system will refuse to measure osmolarity until a new chip is inserted. It is important to ensure use of a new chip for each test because proteins adsorb and salt crystals form on the electrodes after evaporation has run its course, which corrupt the integrity of the measuring electrodes.

Figure 12:
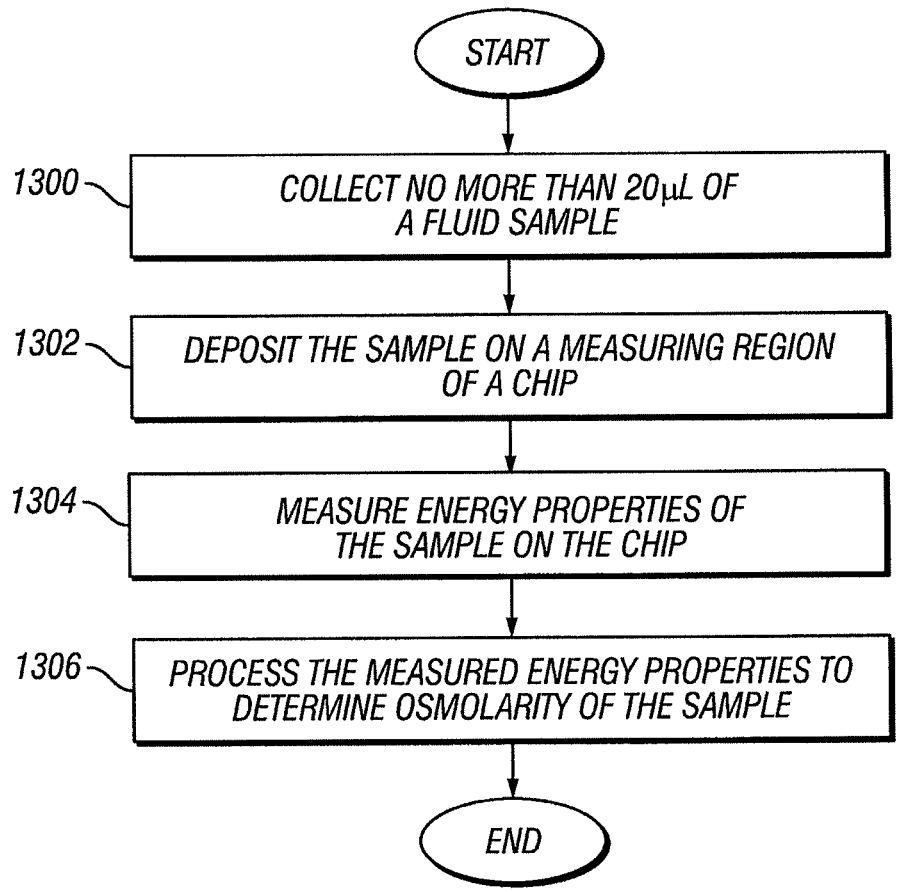
FIG. 12 is a flowchart describing an exemplary osmolarity measurement technique in accordance with the invention.

FIG. 12 is a flowchart describing an exemplary (osmolarity measurement technique in accordance with the invention. A body fluid sample, such as a tear film, is collected at box 1300. The sample typically contains less than one microliter. At box 1302, the collected sample is deposited on a sample region of the chip substrate. The energy properties of the sample are then measured at box 1304. The measured energy properties are then processed, at box 1306, to determine the osmolarity of the sample. If the chip operates in accordance with electrical conductivity measurement, then the measurement processing at box 1306 can include the "electrode oxidation" operation described above that renders the chip electrodes inoperable for any subsequent measuring cycles.

In the measurement process for a conductivity measuring system, a substantially instantaneous shift is observed from the open circuit voltage to a value that closely represents the state of the sample at the time of collection, upon placement of a sample tear film on an electrode array of the substrate. Subsequently, a drift in the conductivity of the sample will be reflected as a continual change in the output.

The output of the measurement chip can be a time-varying voltage that is translated into an osmolarity value. Thus, in a conductivity-based system, more information than just the "electrical conductivity" of the sample can be obtained by measuring the frequency response over a wide range of input signals, which improves the end stage processing. For example, the calibration can be made over a multiple frequencies (e.g., measure ratio of signals at 10, 20, 30, 40, 50, 100 Hz) to make the measurement process a relative calculation. This makes the chip-to-chip voltage drift small. The standard method for macroscale electrode based measurements (i.e. in a pH meter, or microcapillary technique) is to rely upon known buffers to set up a linear calibration curve. Because photolithography is a relatively reproducible manufacturing technique, when coupled to a frequency sweep, calibration can be performed without operator intervention.

As mentioned above, the processing of the energy properties can be performed in a neural network configuration, where the seemingly disparate measured data points obtained from the energy properties can be used to provide more accurate osmolarity reading than from a single energy property measurement. For example, if only the electrical conductivity of the sample is measured, then the calibration curve can be used to simply obtain the osmolarity value corresponding to the conductivity. This osmolarity value, however, generally will not be as accurate as the output of the neural network.

The neural network can be designed to operate on a collection of calibration curves that reflects a substantially optimized transfer function between the energy properties of the sample fluid and the osmolarity. Thus, in one embodiment, the neural network constructs a collection of calibration curves for all variables of interest, such as voltage, evaporation rate and volume change. The neural network can also construct or receive as an input a priority list that assigns an importance factor to each variable to indicate the importance of the variable to the final outcome, or the osmolarity value. The neural network constructs the calibration curves by training on examples of real data where the final outcome is known a priori. Accordingly, the neural network will be trained to predict the final outcome from the best possible combination of variables. This neural network configuration that processes the variables in an efficient combination is then loaded into the processing unit residing in the measurement chip 701 or the base unit. Once trained, the neural network can be configured in software or hardware.

The ability to identify and subtract out manufacturing defects in the electrodes prior to osmolarity testing can also be important. This too can be accomplished via calibration of an osmolarity calibration device that comprises an osmolarity chip, such as chip 1200 illustrated in FIG. 2. This type of calibration can also be achieved, possibly in a more efficient manner, through the use of neural networks, but it will be understood that such networks are not necessary to achieve the calibration processes described in the following description.

Classically, bare metal electrodes were considered poor measuring devices when placed in direct contact with an electrochemical solution of interest. Foremost, there can exist a double layer of counter ions that surround the electrode at the metal/solution interface that can impose a field of sufficient magnitude to significantly alter the ion quantity of interest. In bulk solutions, convection currents or stirring can disrupt these distributions and cause time varying noise, whose magnitude is on the order of the relevant signal. Further, the polarizability and hysterisis of the electrodes can cause problems if sourcing small signals to the electrodes. Finally, large DC or low frequency AC sources from the electrode can also cause irreversible electrolysis that results in bubbling and oxidation of important biological species. Bubbles introduce variable dielectric shifts near the electrode and invalidate inferences drawn about the solution from voltages measured under such conditions.

A conventional solution for these effects is to physically separate the electrodes from the solution through a salt bridge, whereupon bubbling and other nonlinearities in the immediate vicinity of the active electrodes are largely irrelevant to the steady state distribution of ions that flow far from the electrodes. As an example, in devices configured to measure the pH of a solution, the metal electrodes can be separated from the bulk solution with a semipermeable membrane such as glass or ceramic material. Moreover, the metal electrode within the semipermeable membrane is generally comprised of Ag (silver) or calomel (mercury) immersed in a silver chloride or mercurous chloride solution. This allows a single chemical reaction to dominate action close to the electrode. The reaction can be kept close to equilibrium, and when a gradient of ions is created across the semipermeable membrane, an osmotic force is transmitted to the electrode surface through the symmetric redox reaction which drives the system back towards equilibrium. In this way, ions are balanced at the glass-solution and electrode-buffer interface, and nonlinearities can be minimized.

In contrast to typical measurement systems, however, clinical measurements of human tear film osmolarity require far smaller electrodes than traditional systems. This is due to the fact that tens of nanoliters represent the maximum viable collection volume from patients with, e.g., keratoconjunctivitis sicca. As described above, the systems and methods described herein can allow for a clinical device for tear measurements that can meet the strict requirements for accurate measurements and diagnosis in this area by using bare metal electrodes printed on a microchip, e.g., as shown in FIG. 1 and FIG. 2. As a result, none of the traditional solutions to electrode shielding are feasible for such devices because the physical dimensions are far too small. At, for example, 80 μm in diameter, the photolithographed electrodes preclude membranes from being manufactured in a cost effective manner. For example, a spin coated gel permeation layer is prohibitively expensive, results in a low yield process, and introduces several manufacturing variances. Further, osmotic perturbations due to salt bridge gradients would overwhelm the minuscule sample volume of interest. Therefore, many of the typical methods for taking measurements with macroscale electrodes cannot be applied to microelectrodes, and additional issues of calibration remain.

In order to establish a linear calibration profile, where input directly scales with output, conventional macroscale electrodes are typically immersed in multiple known standards. For instance, pH meters will use a set of three buffers at pH 4, 7 and 10, with each fluid marking a point for the fitted line. Between each calibration point, the macroscale electrode can be washed and dried to ensure that the standards do not mix. If one assumes that the electrode buffer inside the glass chamber is of a certain concentration, then calibration can be performed with as little as one standard point. Over time however, the once homogeneous electrode buffer becomes contaminated with the substances it has measured, which then requires at least a two-point calibration in order to be precise.

When working with microelectrodes, however, conventional calibration steps, such as those described above, are often impossible to perform without risking damage to the array and compromising any ensuing measurements. For instance after a calibration standard has been placed on the chip, it is impractical to clean the array with paper, because scratches on the electrode surface will result in exceedingly high current densities at the scratch edge, which then leads to bubbling and invalid measurements. Furthermore, if one were to use a model of human tears for the calibration standard, i.e. with 10 mg/ml BSA as a constituent, protein adsorption to the electrode surface would corrupt the purity of a clinical measurement. Finally, if a small amount of salt solution was used to set calibration points, the fluid would evaporate, leaving a very noticeable salt crystal upon random parts of the chip surface. This residual salt will then dissolve into any subsequent sample that is placed on the chip, and unlike the volume independence displayed by conductivity, slight differences in the amount of fluid deposited as a standard will result in different amounts of salt added to the fluid sample of interest.

Ultimately, a clinical test for dry eye requires a conversion from the relative motion of ions in solution to an absolute osmolarity that can be compared between tests over time. The final value must be independent of the measuring device and stable over time to qualify for diagnostic purposes. Accordingly, the ability to calibrate a microelectrode array, such as those described above, can be hampered by several remaining challenges when attempting to obtain the strictest possible tolerances for the measuring device.

As described below, however, several approaches can be used to calibrate a microelectrode array, such as those described above, in accordance with the systems and methods described herein. These approaches can each start by determining an intrinsic conductivity for each electrode in the array. This intrinsic conductivity can then be stored and used to subtract out the effect of the intrinsic conductivity form final measurements of the electrical properties of a test fluid, such as a tear. Depending on the embodiment, a standard may or may not be used in determining a calibration factor for the electrodes. Further, when a standard is used, a subsequent washing step may or may not be included.

It should also be pointed out that the various approaches can be combined in a modular fashion to produce ever more accurate calibration results. The approaches can thus be used tiered to produce successive levels of intricacy in order to minimize variability between tests.

Figure 13:
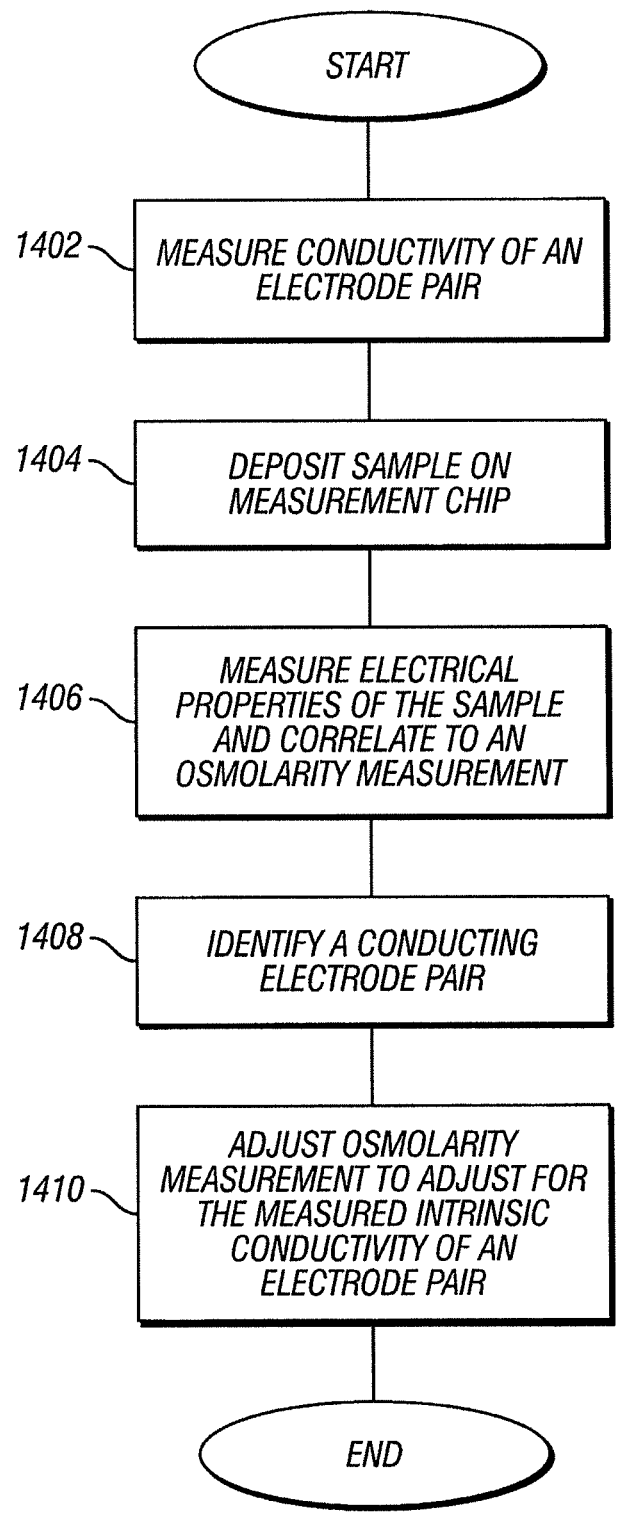
FIG. 13 is a flow chart illustrating a method for calibrating an osmolarity measuring system in accordance with another example embodiment of the invention.

FIG. 13 is a flow chart that illustrates one embodiment of a method for calibrating an osmolarity measuring device that does not use a standard in accordance with one embodiment of the systems and methods described herein. At box 1402, the intrinsic conductivity of the electrodes is measured. The measured intrinsic conductivity for each electrode can then be stored on a memory. At box 1404, a sample fluid of interest, such as a tear film, is introduced to the measuring device, and the electrical properties of the sample fluid are measured at box 1406. In one embodiment, the processing circuitry also identifies the electrodes from the electrode array that are in contact with the sample fluid at box 1408. The electrodes that are in contact with the sample fluid are conducting electrodes, and the identity of the conducting electrodes can also be stored in memory. At box 1410, the processing circuitry adjusts the measured electrical properties of the sample fluid to adjust for the intrinsic conductivity of the electrodes, on a pair-wise basis, that performed the measurement of the sample. This adjustment results an osmolarity measurement of the sample alone, and is independent of variances in the thickness of electrode metalization, dielectric deposition, and other variances in the electrodes that can occur during manufacturing of the measuring device.

The intrinsic conductivity can be determined (box 1402), in one embodiment, by applying a DC current to the electrode array and measuring the resulting output voltage for each electrode. The corresponding resistance can then be calculated based on the DC current and the output voltage and, e.g., stored in memory. In an alternative embodiment, a more complex signal, e.g., a sinc wave, can be generated in the time domain and applied to the array of electrodes. The corresponding outputs can then be measured and stored. A Fourier transform can then be applied to the stored output data. The result is a map of amplitude versus frequency that indicates the relative conductance over a range of frequencies for each electrode. This map can be generated for a range of frequencies of interest for a particular implementation, e.g., from the low kHz to the MHz range.

In order to deliver a current signal to each electrode and measure the resulting output for calibration purposes, two leads can be provided for each electrode. The current signal can then be applied and the output measured, for a given electrode, via the two leads.

In such an embodiment, the slope of the resulting calibration curve can be assumed to be constant over time. The curve can then be built into a osmolarity measurement device, such as those described above. Adjustments to the osmolarity determinations can then be made through electrode resistance subtraction, which will simply shift the input mapping along the x-axis of the calibration curve. Other effects, such as humidity and ambient temperature effects can then, depending on the embodiment, be accounted for in subsequent signal processing.

The ability to map out the intrinsic conductivity of each electrode pair prior to testing also gives a confidence bound to the array locations. In this manner, the electrode is defined as a random process of gaussian random variables with a sample mean and variance as defined by the conductivity calculations above. Any electrode outside the 95th percentile of the expected variance can be considered flawed, and its signals can be neglected in future calculations. This ability to selectively address electrode pairs in an array enhances the ability to calibrate the reading and protect against spurious manufacturing defects.

As an example, it should be remembered that the electrode array of FIG. 2 provides a means to measure the size of, e.g., a tear droplet 202 by detecting the extent of conducting electrodes 208 to thereby determine the extent of the droplet. In particular, processing circuitry can determine the number of electrodes that are conducting, and therefore the number of adjacent electrodes that are covered by the droplet 202. The identities of the electrodes from the array that are conducting and in contact with the sample fluid 202 can then stored in memory.

Thus, following the completion of the sample testing, the intrinsic conductivity of all of the conducting electrode pairs can be subtracted from the sample output signal to calculate an osmolarity value indicative of the sample alone. In one embodiment, it is important to recognize that the sample fluid 202 will not cover all electrodes in the array. Therefore, only those electrodes that are conducting and in contact with the sample fluid 202 are included in the calculation to adjust the sample measurement. As mentioned, the resulting osmolarity measurement of the sample fluid 202 is therefore made independent of variances in the thickness of electrode metalization, dielectric deposition, and other variances that may occur during manufacturing for the conducting electrodes that perform the measurement.

While the systems and methods from calibration just described are useful and simple to implement, requiring minimal software post processing to accomplish any needed correction, it is unlikely that this method will detect sharp deformities in electrode geometries such as metal peaks or rough edges because these defects will not significantly alter the intrinsic conductivity of the electrodes. It can be shown that the bare metal electrodes described above suffice for measurement when high frequency sine waves are used as input signals to the microelectrodes. Even at 10 V peak to peak, 10-100 kHz waves do not initiate bubbling in the aliquot of tear film sample that is being measured. This is can be due to the fact that within this frequency range, there is a balance between water polarizability and ionic mobility, resulting in oscillations of ions rather than bulk movement. This solves many problems with electrolysis and other DC electrode problems. However, when a sample fluid is applied, electrode geometries such as metal peaks or rough edges may cause bubbling and mar the measurement. Therefore, in order to account for these effects, it is useful to begin each test with a one- or two-points standard calibration prior to use.

Figure 14:
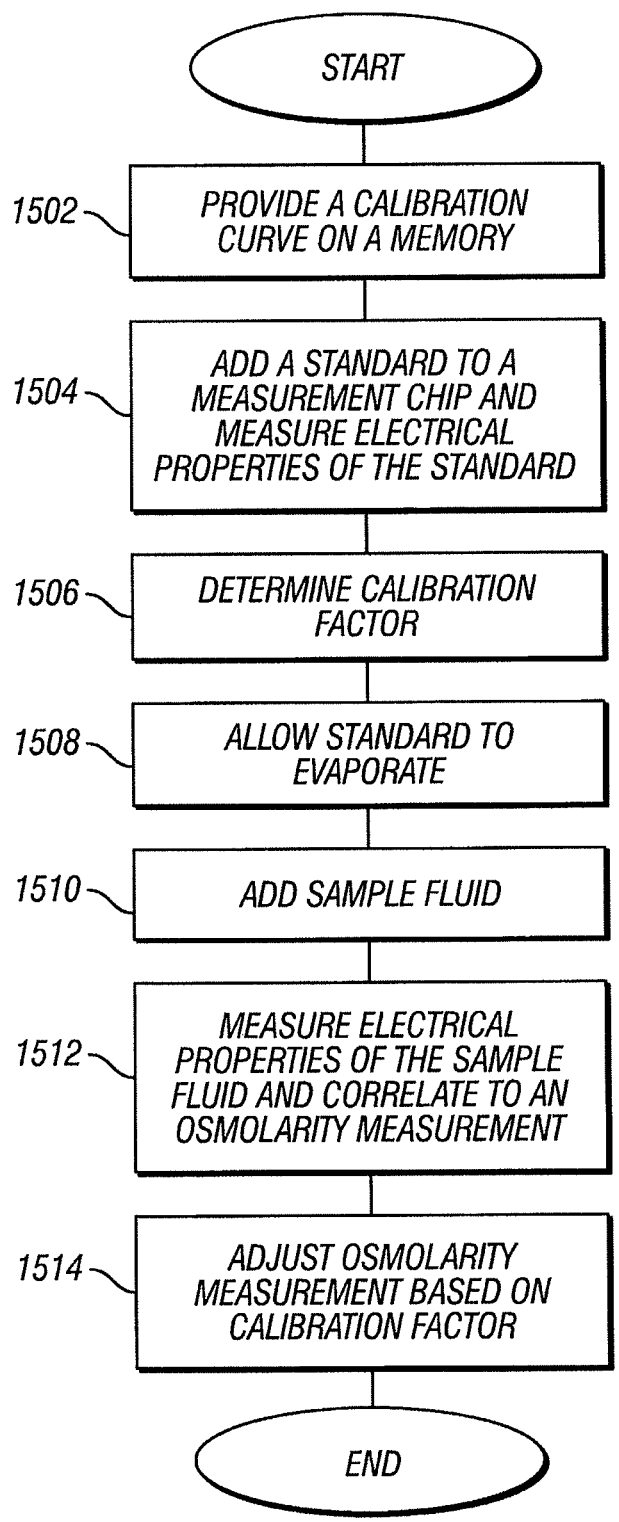
FIG. 14 is a flow chart illustrating a method for calibrating an osmolarity measuring system in accordance with another example embodiment of the invention.

FIG. 14 is a flow chart that illustrates one embodiment of a method for calibrating an osmolarity measuring device with a standard fluid. At box 1502, a calibration curve is provided on a memory, and the calibration curve is assumed to be a straight line. One point of the line is obtained through the assumption that when the measured electrical properties of the standard are equal to zero, the osmolarity of the standard is equal to zero. The electrical properties (i.e. sinc wave Fourier transform, etc.) of the high end of the concentration range, around 500 mOsms, can then be predefined in memory based on known electrical properties for a fluid having a known concentration.

At box 1504, a standard fluid can be deposited onto the microelectrode array of a measuring device, and the electrical properties of the standard can be measured at box 1504. The methods for measuring the electrical properties of the standard fluid can include the methods described above for measuring the electrical properties of a sample fluid. A processing device can then be configured to correlate the measured electrical properties to an osmolarity value and, e.g., store the osmolarity measurement of the standard fluid in memory.

In one embodiment, the standard fluid that is added at box 1504 comprises a small aliquot, for example, 1 μL, of deionized water. The osmolarity measurement for deionized water can be registered as a lower bound on the calibration curve since deionized water exhibits a minimum amount of osmotic character. In one embodiment, a one-point calibration is used such that the entire range for the measurement scale of the device can be extrapolated based on the difference between the expected osmolarity of deionized water and the actual measured osmolarity of the standard. At box 1506, the processing device determines a calibration factor to adjust the slope of the measurement scale to match the calibration curve. Further, any adjustments to the slope of the measurement scale are made with the measured fluid per electrode pair, such that the final value from each electrode pair is equivalent with all others. The final calibration factor can then be stored in memory.

After calibration has been determined, the standard can be allowed to evaporate from the microelectrode array at box 1508. Evaporation can be necessary to prevent the standard from mixing with and corrupting the sample fluid. Deionized water provides an exemplary standard when the deionized water has such low salt content that there is no salt crystal deposited on the chip after evaporation.

In one embodiment where there is no salt crystal remaining after the standard evaporates, the sample fluid to be tested can then be deposited on the microelectrode array of the measuring device at box 1510. The microelectrode array transfers energy to the sample fluid and enables the detection of the sample fluid's electrical properties, which are mapped to an osmolarity measurement at box 1512 as described above. At box 1514, a processing device can be configured to adjust the osmolarity measurement based on the previously determined calibration factor. The use of the calibration factor results in an osmolarity measurement that is substantially independent from variances in the geometry of the microelectrode array.

The process of FIG. 14 can also be combined with the simpler process of FIG. 13 in order to improve accuracy.

Figure 15:
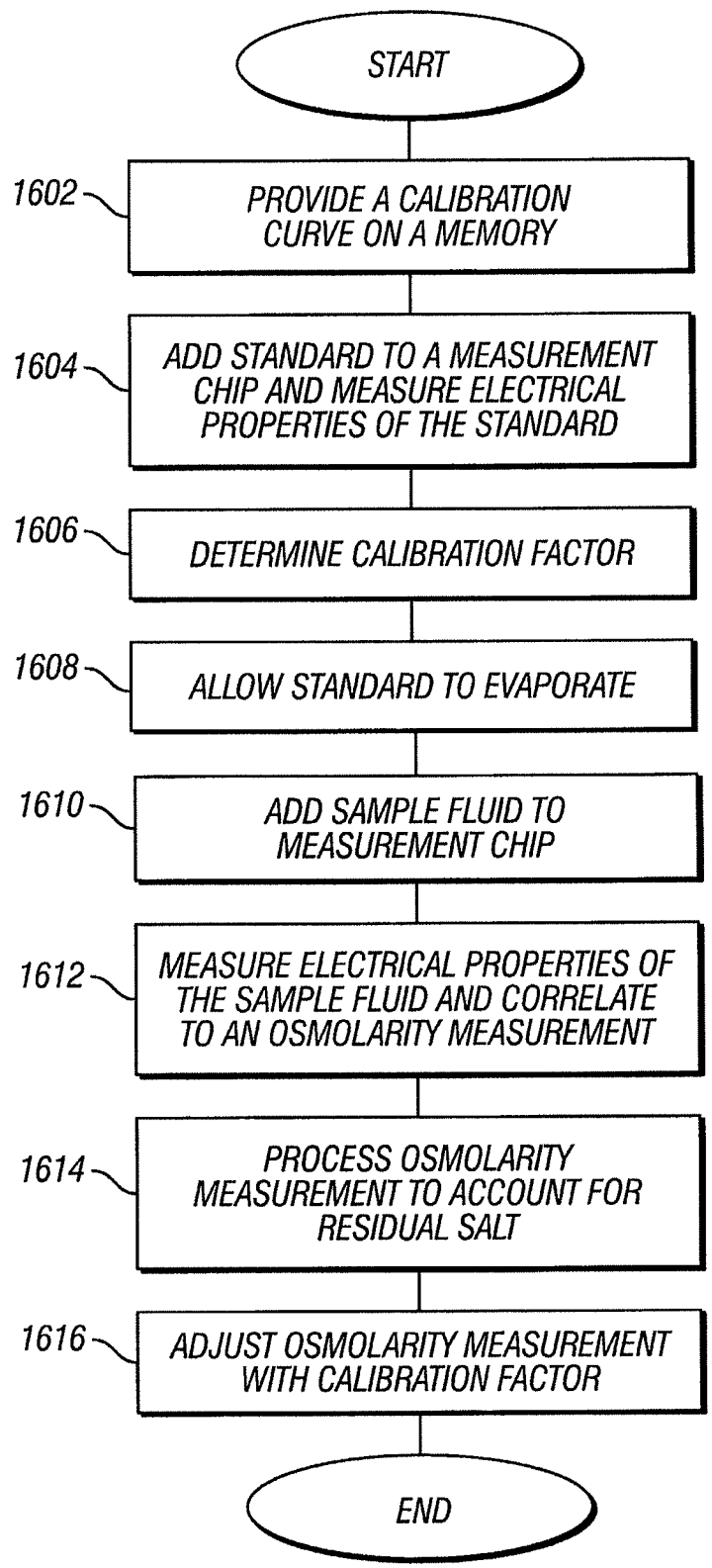
FIG. 15 is a flow chart illustrating a method for calibrating an osmolarity measuring system in accordance with another example embodiment of the invention.

FIG. 15 is a flow chart that illustrates another embodiment of a method for calibrating an osmolarity measuring device using a standard fluid that is a slat solution. At box 1602, a calibration curve can be provided on a memory, and the calibration curve can be assumed to be a straight line. One point of the line is obtained through the assumption that when the measured electrical properties of the standard are equal to zero, the osmolarity of the standard is equal to zero. The electrical properties of the high end of the concentration range, around 500 mOsms, can be predefined in memory based on known electrical properties for a fluid having a known concentration.

At box 1604 a standard fluid can then be deposited onto the microelectrode array of a measuring device, and the electrical properties of the standard can be measured. The methods for measuring the electrical properties of the standard can, for example, include the methods described above for measuring the electrical properties of a sample fluid. A processing device can then be configured to correlate the measured electrical properties to an osmolarity value, and store the osmolarity measurement of the standard on a memory.

At box 1606, the processing device can be configured to then determine a calibration factor to adjust the slope of the measurement scale to match the calibration curve. Further, any adjustments to the slope of the measurement scale can be made with the measured fluid on a per electrode pair basis, such that the final value from each electrode pair is equivalent with all others. The final calibration factor can then be stored in memory.

Figure 16:
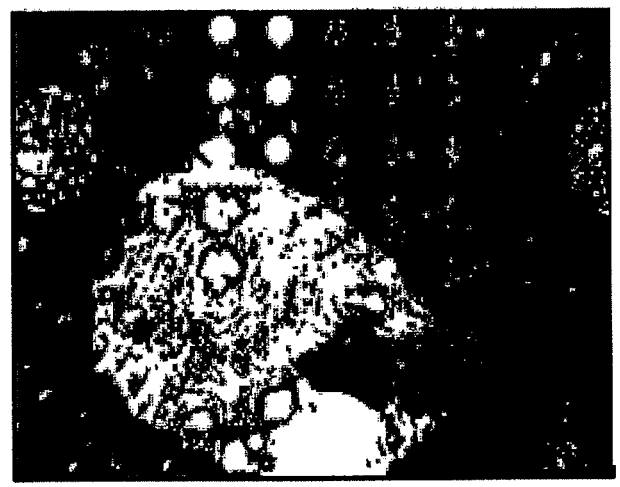
FIG. 16 is an image showing residual salt crystals on a miroelectrode array.

In this process, however, the standard can be a simple salt solution (NaCl), or a complex salt solution, e.g., with sodium, potassium, calcium and magnesium salts in physiological ratios. However, when the salt solution evaporates at box 1608, a very noticeable salt crystal will often remain on the chip surface as shown in FIG. 16. When this occurs, the left over salt crystal should be accounted for in the subsequent osmolarity measurement that is made at box 1612.

Figure 17:
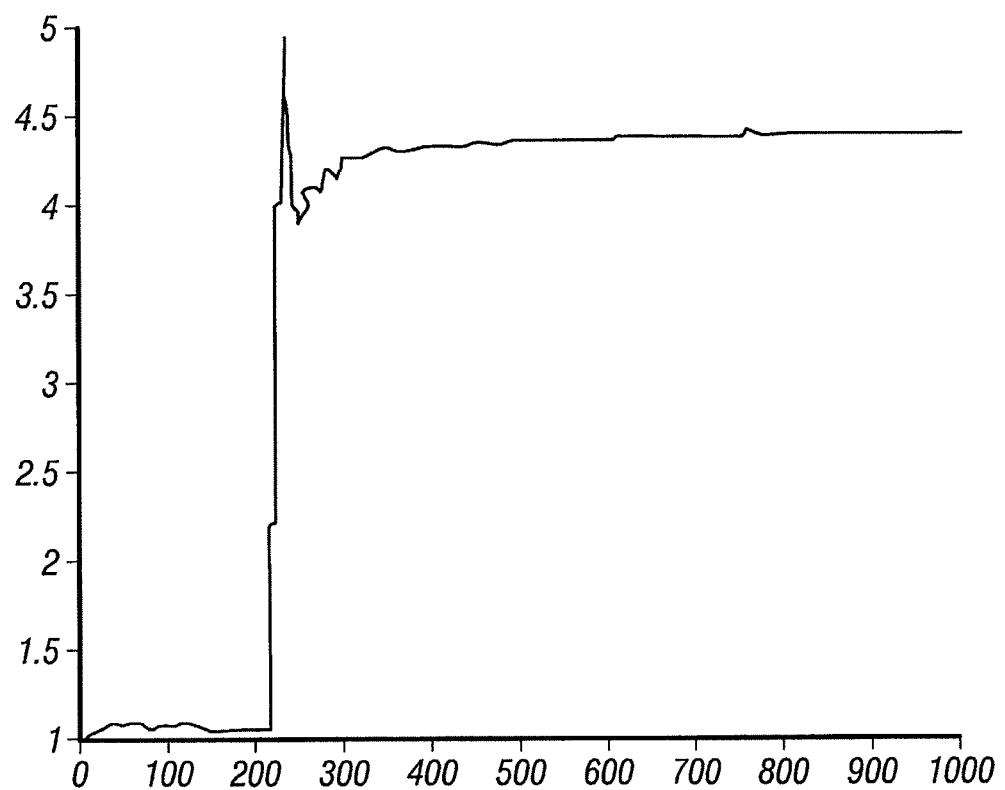
FIG. 17 is a graph illustrating a typical response when a sample fluid is introduced to a microelectrode array.
Figure 18:
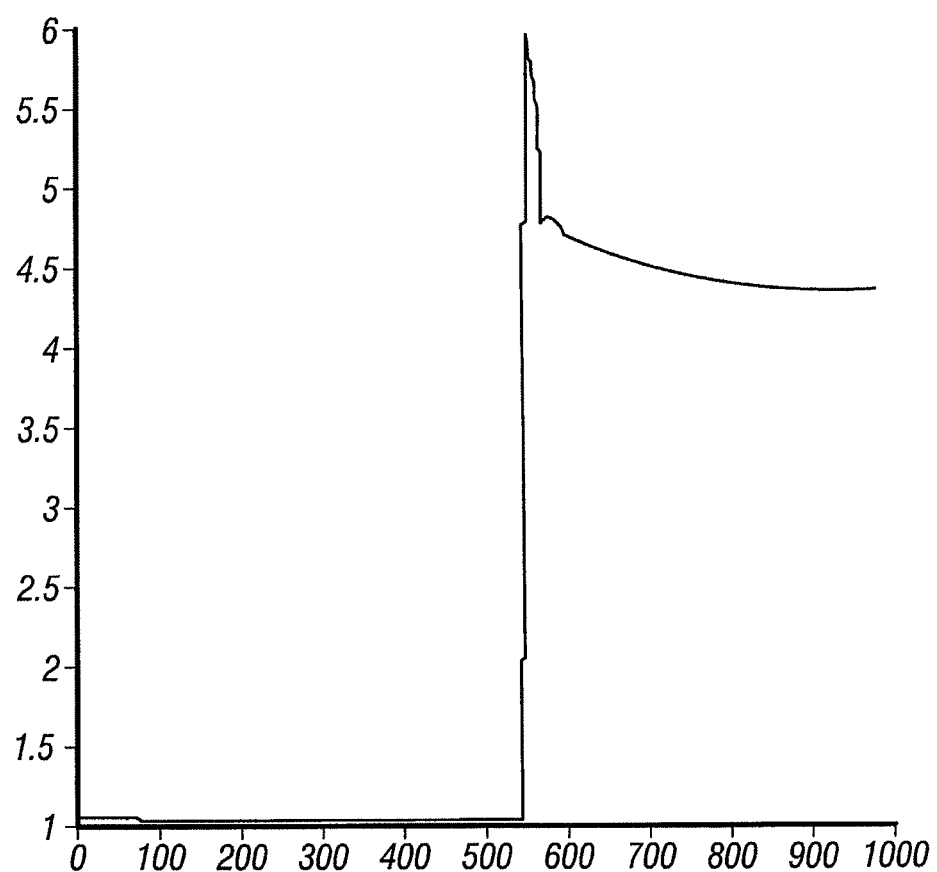
FIG. 18 is a graph illustrating a response when a sample fluid is introduced to a microelectrode array that contains residual salt.

For example, FIG. 17 demonstrates a typical response when a sample fluid is introduced to a microelectrode array that does not include residual salt. In comparison, FIG. 18 shows the response when residual salt is present on the microelectrode array at the time the sample fluid is introduced. The presence of a salt crystal clearly alters the response, such that it steadily declines for a period before righting itself and heading into the steady evaporation mode. As shown in FIG. 18, the normal second order dynamics are suppressed. This is due to the fact that upon sample placement, the residual salt crystal will begin to dissolve into the sample fluid. The concentration of residual salt near the electrode will continue to decrease until its contribution has become uniformly mixed throughout the sample, whereupon the curve will begin to rise again due to evaporation.

During this transient response, dissolving ions between two measuring electrodes will present a much higher conductivity than in the originally deposited solution FIG. 16 also shows how a misplaced drop of salt solution can differentially cover the array surface, which means that the signal between pairs of electrodes will be vastly different depending on their proximity to the salt crystal.

Therefore, in another embodiment of the systems and methods for calibrating an osmolarity measuring device, a processing device can be configured to mathematically eliminate the effects of any residual salt crystals from the osmolarity measurement of the sample at box 1614. The effects of the residual salt crystal can, for example, be eliminated by integrating the descending curves from every electrode pair, which estimates the amount of salt added to the solution. The estimation of the amount of salt that is added is accomplished by summing only the area above the steady state line, which is determined by a linear regression far from the time point of sample delivery. These effects are then subtracted out from the total volume of the sample. As previously discussed, the total volume of the sample can be estimated by the processing device based on the number of electrodes that are in contact with the sample.

Based on these parameters, the measured concentration of the sample is adjusted directly. The concentration of the sample is based on the number of ions per unit of volume. The osmolarity measurement provides the total number of ions from the sample plus the residual salt crystal, and the processing device estimates the volume of the sample. Accordingly, the adjustment requires the subtraction of the number residual salt ions from the measured number of total ions in the sample. The number of residual salt ions is determined through the integration method discussed above. This method enables the use of a salt solution standard on the microscale without the need for expensive washing hardware. After the effect from the residual salt has been subtracted, the processing device adjusts the resulting osmolarity measurement based on the previously determined calibration factor at box 1514. The use of the calibration factor results in an osmolarity measurement that is substantially independent from variances in the geometry of the microelectrode array.

Figure 19:
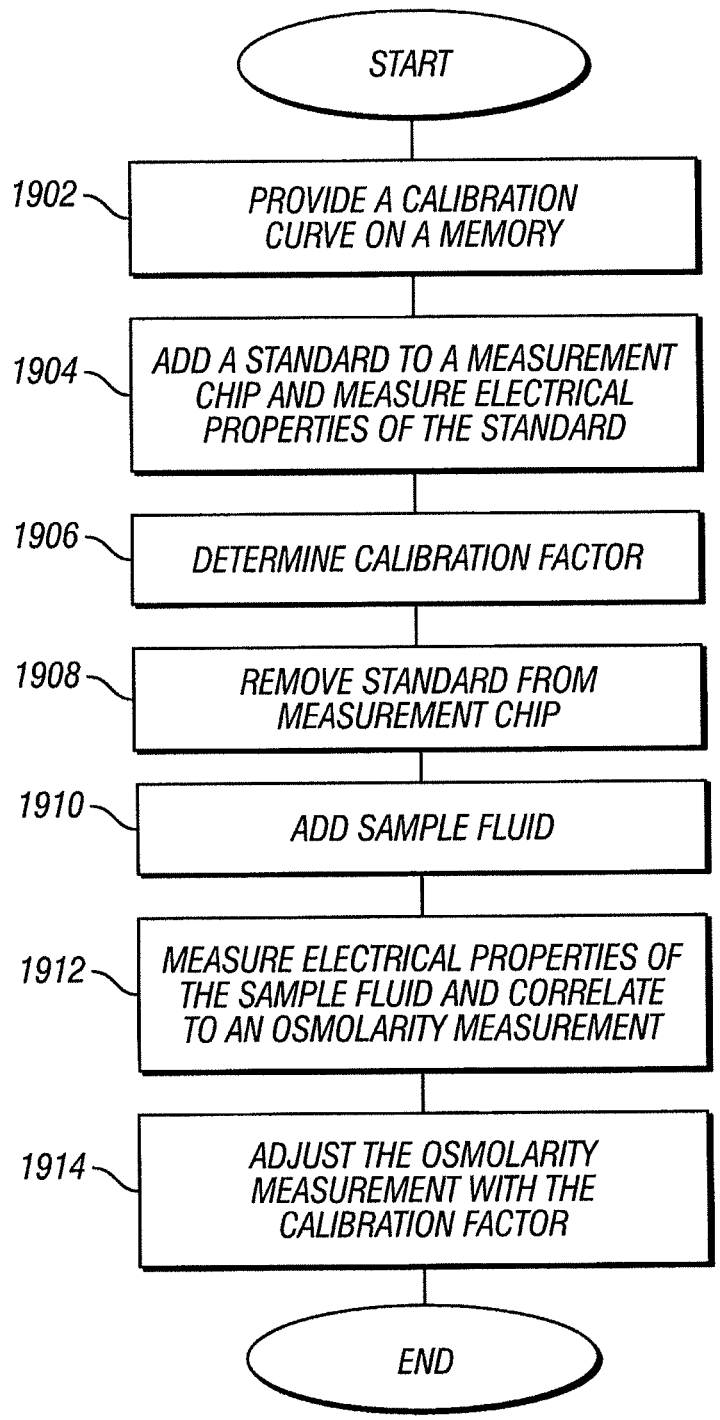
FIG. 19 is a flow chart illustrating a method for calibrating an osmolarity measuring system in accordance with another example embodiment of the invention.

FIG. 19 is a flow chart that illustrates still another embodiment of a method for calibrating an osmolarity measuring device with a standard fluid in accordance with the systems and methods described herein. In the embodiment of FIG. 19, a wash can be used in conjunction with the application of a standard fluid. The steps performed at boxes 1902, 1904, and 1906 have been previously discussed and result in the determination of a calibration factor based on the measurement of one or more standards. In one embodiment, the standard contains a simple salt solution (NaCl), or a complex salt solution, with sodium, potassium, calcium and magnesium salts in physiological ratios).

At box 1908, an action is performed to remove the standard from the chip before the standard evaporates and prevent the accumulation of residual salt on the chip. In one embodiment, the washing step uses a microfluidic chamber attached in series to the sample receiving substrate to allow a steady stream of deionized water to flow across the chip surface. Once a standard aliquot has been deposited, either through a perpendicular microfluidic flow channel or by manual methods, and the (calibration measurement has been made, the washing apparatus will flow deionized water across the electrode surface until the conductivity has reached a steady state commensurate with the expected deionized water levels. The steady state conductivity indicates that the chip surface has been cleaned of any standard and is ready to accept a sample. The flow is halted and the deionized water is allowed to evaporate on the chip surface, ideally leaving no salt crystal behind.

In another embodiment, a valved high pressure air supply can be implemented to remove the standard. The tube is connected to the air supply and placed in close proximity to the receiving substrate and at an acute angle from the surface. The angle is such that a quick puff of air from the tube forces any fluid from the surface of the chip to be cleared completely from the substrate. The flow of air is triggered upon completion of the calibration measurement. The resulting air flow may be pulsed several times until the signal at each electrode pair has returned to open circuit values. In another embodiment, air supply is combined with the microfluidic washing stage to eliminate the need to evaporate fluids from the surface of the chip.

Furthermore, multipoint calibrations may be performed if a complete washing apparatus is attached to the chip surface, where deionized water and increasingly concentrated salt solutions are deposited, or flowed, onto the chip surface, and then a puff of air is used to clear the array. At boxes 1912 and 1914, the sample fluid is deposited onto the micro electrode array and the calibrated osmolarity measurement is completed in the methods that have been previously discussed.

Biomarker Normalization

In most patients who suffer from dry eye syndrome (DES), ocular allergy, general or ocular infections, blepharitis, diabetes, or other diseases in which DNA or other molecular biomarkers are present in tears, there is a clear clinical need for the ability to analyze nanoliter amounts of tears collected from the lower tear lake.

Nanoliter tear samples are necessary to minimize the time of residence of a collection device within the tear lake, which lowers the chance of inducing reflex tearing, a situation in which hypo-osmolar (less concentrated, very watery) tears are flushed onto the ocular surface, thereby reducing the available biomarker concentrations and introducing diagnostic variability within the clinical routine. As the amount of reflex tearing is disease-specific and patient-specific, the amount of dilution varies with stimulation. Historically, tear collection protocols suggest collecting relatively large volumes of tears, typically several microliters of tears, in order to collect a sufficient sample volume to conduct standard in vitro diagnostic tests. These biomarker assays often take upwards of thirty minutes of continual tear sampling to attain such high volumes. Older patients, and especially those with DES, often present less than 200 nL of available tears in the tear lake for sampling at a given time. Thus, tear collection for standard in vitro tests is uncomfortable and moderately invasive.

Hypo-osmolar tears can result from a variety of conditions. An overabundance of non-lubricating tears can occur in certain dry eye subtypes; known as epiphora, these patients may have occluded nasolacrimal ducts which increase tear residence time within the tear lake.

Patients with DES are also known to have a dysfunction of the tear film that can result in a hyper-osmolar tear. Whether through aqueous deficiency or meibomian gland disease, the steady state equilibrium concentration of tears is significantly increased in DES patients. Some DES patients are known to have steady state tear lake concentrations approximately 30%-50% higher than age-matched normals (healthy subjects). Measured osmolarities of 400 mOsm/L in the tear lake of severe DES patients have been frequently reported. Hyperosmolar tears are also observed in contact lens wearers. Regardless of contact lens material or the type of lens worn, contact lenses disrupt the preocular tear film and shift the homeostasis of tears towards a hyper-osmolar state.

Post-LASIK patients and DES patients may also have varying levels of innervation and/or nerve function, which affect the ability to produce reflex tearing. In vitro diagnostics performed on these types of patients may therefore report quite different concentrations of biomarkers depending on the state of the patient and the manner in which tears are collected. There is a clear need for in vitro diagnostic methods that can eliminate the variability introduced by tear sampling and from hypo-osmolar and hyper-osmolar tear film concentrations.

Recently, a new class of microfluidic technologies have greatly reduced the volume requirements for in vitro diagnostics, wherein submicroliter samples can be used to test for biomarkers within tears. Because the tears offer an ideal, largely acellular biological matrix from which to perform various in vitro diagnostics, collecting tears may now be of interest to many doctors and medical professionals who are less familiar with working near the ocular surface, and who may unknowingly cause undue reflex tearing during tear collection. The undue reflex tearing from such sampling can cause inaccurate diagnostic results. This problem reinforces the need for techniques of measuring biomarker concentrations in tears that are independent of sampling.

In accordance with the present invention, biomarker normalization is performed against a measured osmolarity in order to remove the impact of tear sampling and patient-specific tear homeostasis from the interpretation of biomarker concentration in tears. The normalization provides an Adjusted Tear Biomarker Level.

Traditional measurement of tear biomarkers such as immunoglobulins (IgE, IgA, IgG, IgM), glucose, insulin levels, lactoferrin, tear lysozyme, cytokines, hormones, hormone metabolites, infectious disease phenotypes, nucleic acids, proteins, or lipid fractions, are carried out without the simultaneous analysis of tear osmolarity. Traditional means of measuring tear osmolarity are incompatible with tear biomarker analysis. In accordance with the present invention, a receiving substrate, sample region, and energy transduction mechanism within a nanofluidic channel provide for the first time, the possibility of measuring tear osmolarity on the same undiluted tear sample as the biomarker. The combination of an integrated tear collection interface and transducer provides leverage against evaporation following sampling.

The calculation of an Adjusted Tear Biomarker Level is as follows. Normal tear osmolarity is generally accepted to be near 300 mOsm/L (with ranges from 280-316 mOsm/L). The Adjusted Tear Biomarker Level can be obtained from the following equation:

Adjusted Tear Biomarker Level=(300 mOsm/L*Measured Tear Biomarker Level)/(Measured Tear Osmolarity Level)

The defined value of 300 mOsm/L can be substituted for any of the appropriate range of tear osmolarity levels. In another embodiment, the basal level of tear osmolarity can be measured for a specific patient at the beginning of a study, at pretreatment, at an early age, or prior to surgery in order to establish a personalized baseline level of tear homeostasis. Following the passage of time, a pharmaceutical administration, or surgery, the personalized baseline level can be substituted for the defined 300 mOsm/L.

Figure 20:
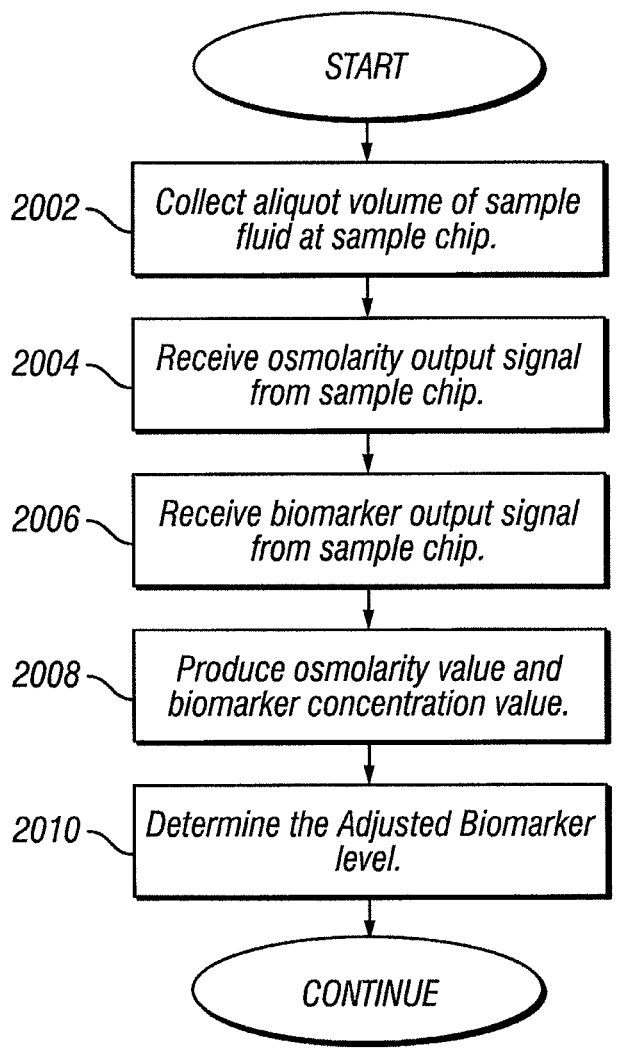
FIG. 20 is a flow chart illustrating biomarker normalization in accordance with the invention.

FIG. 20 is a flowchart that illustrates processing in accordance with the normalization technique described herein. Initially, at the box numbered 2002, an aliquot volume (such as a nanoliter tear volume) of sample fluid is collected to a sample region of a sample chip. Next, at box 2004, an osmolarity output signal is received from the sample region that indicates energy properties of the sample fluid, wherein the osmolarity output signal is correlated with osmolarity of the sample fluid. Next, at box 2006, a biomarker output signal is received from the sample region that indicates chemical properties of the sample fluid, wherein the biomarker output signal is correlated with biomarker concentration of the sample fluid. Next, at box 2008, the osmolarity output signal is processed to produce an osmolarity value for the sample fluid and the biomarker output signal is processed to produce a biomarker concentration value for the sample fluid. The processing can be performed simultaneously or serially. Lastly, at box 2010, the Adjusted Biomarker Level is determined, which provides normalization of biomarker concentration values. As noted above, the adjusted level provides a normalization of biomarker concentration values and can correct for patient-specific tear homeostasis and clinician induced tear sampling variance in connection with obtaining the sample fluid.

The operations depicted in FIG. 20 can be performed by any of the system embodiments illustrated in the drawings (FIGS. 1-11) with a processor configured to perform the normalization operations as described herein.

If desired, open loop adjustment is also possible, where the 300 mOsm/L constant is unused, as in the following equation:

Open Loop Adjusted Tear Biomarker Level=Measured Tear Biomarker Level/(Measured Tear Osmolarity Level)

An advantage of using a standard or personal baseline osmolarity value to normalize against is that the Adjusted Tear Biomarker Level is expressed in units identical to the Measured Tear Biomarker Level. Open loop adjustment would result in a Biomarker Level/mOsms/L, which could be a more difficult parameter for clinicians to interpret, especially if the analyte of interest is commonly known to have a range in unnormalized units.

Similar Adjusted Tear Biomarker Levels can be performed using linear, logarithmic, exponential, or through the use of calibration curve adjustments. For example, a linear adjusted Tear Biomarker Level could take on the form given by:

Linear Adjusted Tear Biomarker Level=$B_{adj}=B_m*(1+(Alpha*(Osm_m-300 \text{ mOsms/L})))$ where $B_{adj}$ is the Linear Adjusted Tear Biomarker Level, $B_m$ is the measured biomarker level, Alpha is the linear correction factor, and $Osm_m$ is the measured osmolarity. Both the Alpha and the 300 mOsms/L point can be altered to fit the specific biomarker curve.

IgE, for example, is suggested to be found on the order of 50-60 of ng/mL range in unsensitized individuals, and 100-300 ng/mL in patients with vernal, seasonal, or perrenial conjunctivitis (see publications by Nomura, "Tear IgE Concentrations in Allergic Conjunctivitis" in Eye, Vol. 12 (Part 2), 1998 at 296-98; and Allansmith, "Tissue, Tear, and Serum IgE Concentrations in Vernal Conjunctivitis" in Am. J. of Ophthalmology, Vol 81, No. 4, 1976, at 506-11). From Nomura:

> Tear IgE concentrations showed significant increases in the vernal keratoconjunctivitis (322.2+/−45.7 ng/ml), seasonal allergic conjunctivitis (194.7+/−21.7 ng/ml) and perrenial allergic conjunctivitis (134.8+/−23.1 ng/ml) groups when compared with controls (52.1+/−9.7 ng/ml, p<0.01). No significant difference was found between epidemic keratoconjunctivitis (97.2+/−11.7 ng/ml) and bacterial conjunctivitis (92.6+/−13.8 ng/ml) groups and controls (p=0.1).

For DES patients with an elevated osmolarity of 400 mOsm/L, unnormalized determination of the tear IgE levels may easily lead to incorrect interpretation. A more severe bacterial conjunctivitis could easily be mistaken for a relatively mild perrenial allergic conjunctivitis based on unnormalized IgE. Similarly, if a normal patient with seasonal allergic conjunctivitis was overstimulated during tear collection and produced hypo-osmolar reflex tears, their tear IgE levels could easily drop beneath perrenial allergic conjunctivitis indications. Normalizing by measured tear osmolarity prevents this type of misdiagnosis.

Figure 21:
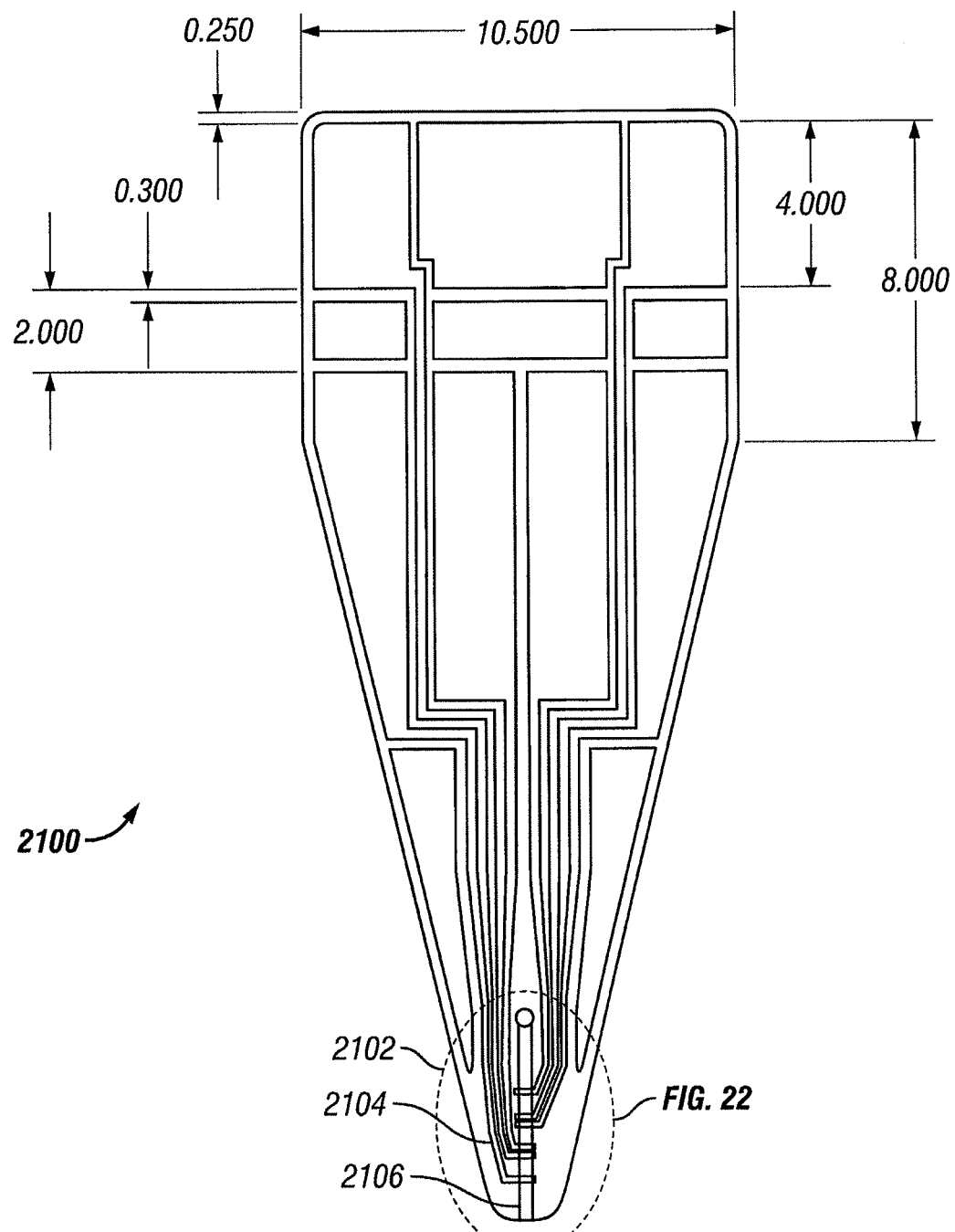
FIG. 21 is a plan view of a receiving substrate in which osmolarity is multiplexed in space with biomarker detection.
Figure 22:
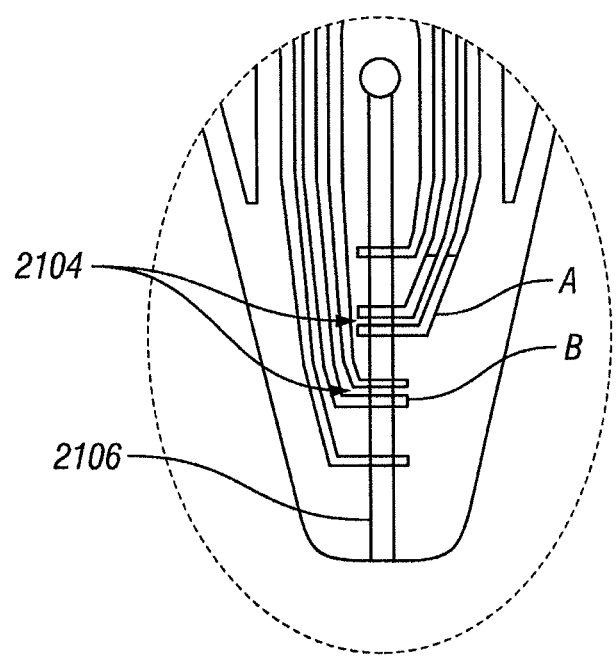
FIG. 22 is a detail view of the FIG. 21 receiving substrate showing the arrangement of electrodes in the sample region.

In one embodiment, a plurality of electrodes contained within the sample region of the receiving substrate can be functionalized with distinct energy transduction mechanisms; one set of electrodes would contain an osmolarity transducer (e.g., a non-polarized metal electrode for impedance analysis of osmolarity such as gold, platinum, and the like, and a conductive polymer such as polypyrrole, polyacetylene, polyaniline, and the like) with another set of electrodes with corresponding surface chemistry to bind antibody, avibody, aptamer, or other receptor for a biomarker ligand. In this embodiment, the osmolarity is multiplexed in space. An example of this embodiment is shown in FIG. 21, which is a plan view of the receiving substrate 2100 showing the sample region 2102. A detailed view of the electrodes 2104 in the sample region 2102 is provided in FIG. 22. The illustrated electrodes 2104 indicate a group of electrodes demarcated within the sample region as group "A" with the biomarker function and gold osmolarity electrodes demarcated within the sample region as group "B" for the osmolarity function. A capillary 2106 receives the sample fluid and distributes the fluid along its length for interaction with the electrodes A and B.

Upon depositing an aliquot volume of sample fluid on the sample region of a substrate (through capillary action, aspiration, or similar techniques), energy imparted into the sample fluid is transduced by the sample region to produce an output signal that indicates the energy properties of the sample fluid that are correlated with the osmolarity of the sample fluid. Simultaneously or in parallel operations, potentiometric, amperometric, pulse voltammetry, cyclic voltammetry, broadband frequency response, impedance, or other electrochemical methods are used to transduce output signals from the electrochemically modified electrodes to indicate chemical properties of the sample fluid that are correlated with the concentration of biomarkers in tears. Thus, the osmolarity and biomarker output signals are generated at the same time but from different sets of electrodes. Subsequently, an Adjusted Tear Biomarker Level is calculated to compensate for the possibility of patient hyperosmolarity or dilution introduced by tear sampling. That is, the Adjusted Tear Biomarker Level can compensate and correct for patient-specific tear homeostasis and for clinician-induced tear sampling variance in connection with obtaining the sample fluid.

In other embodiments where osmolarity is multiplexed in space, optical indicators, such as a plurality of nano-scale spheres having a luminescence correlated to osmolarity of the sample fluid are deposited on a subset of the sample region. Other optical transduction mechanisms can include iontophoretic fluorescent nanoscale spheres, or metal films amenable to surface plasmon resonance. In parallel, subsets of the sample region are configured to produce output signals that indicate chemical properties of the sample fluid that are correlated with the concentration of a biomarker in tear. Sample region subsets can include luminescence, fluorescent, chemiluminescent, resonant energy transfer, optoentropic, surface enhanced Raman, colorimetric, surface plasmon resonant, plasmonic, or other optical indicators commonly used for biomarker transduction. Following illumination by an optical energy source that imparts optical energy into the sample fluid, the optical energy can be transduced by the sample region to produce an optical output signal that indicates the energy and chemical properties of the sample fluid that are correlated with the osmolarity and tear biomarker concentration, respectively. An optical detector then receives the optical output signal from the sample region, and a processing device processes the output signal to produce an estimate of sample fluid osmolarity and biomarker concentration. Subsequently, an Adjusted Tear Biomarker Level is calculated to compensate for the possibility of patient hyperosmolarity or dilution introduced by tear sampling.

In yet another embodiment, electrical, optical, or thermal (e.g., freezing point depression) methods of osmolarity determination within the receiving substrate can be independently combined with electrical or optical methods of tear biomarker concentration detection. For example, conductive osmolarity determinations can be combined with optical transducers for tear biomarker analysis. Spatial multiplexing supports multiple biomarkers in such a format.

In spatial multiplexing embodiments, the measurement of tear osmolarity can either be performed at the same time as the biomarker assays, or serially by modulating the input energy type.

For example, if both osmolarity and tear biomarker analysis are spatially multiplexed via optical methods, then tear osmolarity can be determined by surface plasmon resonance (i.e., the angle atop a metal film) and the tear biomarker can be analyzed by fluorescence.

In another embodiment, electrodes covered with a chromogenic competitive assay system can be interrogated for conductivity in order to determine osmolarity, followed by absorbance of light in order to quantify the concentration of tear biomarker.

If fluorescent nanoscale spheres are used as an osmolarity marker and chemiluminescent reporter antibodies are used to transduce the tear biomarker concentration, then the first input would comprise an appropriate excitation light, and the second energy input would comprise pumping a known concentration of luminescent substrate and fuel across the sample region (e.g., luminol and hydrogen peroxide).

In another embodiment, a "molecular ruler" could be used to transduce the osmolarity, for example, a plasmonic pair of nanoscale metal spheres attached to DNA could indicate the bulk sample fluid osmolarity by the optical detection of absorbance change around 520 nm. In parallel, if fluorescently labeled secondary antibodies are used to label the analyte of interest, the fluorescent response from excitation light would be read following the absorbance of the molecular ruler within the same fluid.

Other combinations of electrical, optical, and thermal transduction can be combined to achieve requisite levels of sensitivity, specificity, and multiplexing while minimizing the need for washing or external interfacing to the sample region.

These methods are generally amenable to spatial multiplexing in a discrete sense, where subsets of the sample region are orthogonal within the surface plane. Such methods are also amenable to vertical spatial multiplexing, where, for example, the biomarker transducer is built atop the osmolarity transducer, as in a fluorescent assay built atop a conductive polymer.

In another embodiment, a plurality of electrodes are configured for electrochemical transduction of the biomarker of interest, and the osmolarity is multiplexed in time. In this embodiment, all the electrodes are functionalized with the same surface chemistry for the biomarker assay. Because there is a diffusion time associated with the ligand binding of the tear biomarker, osmolarity can be determined immediately after introduction into the sample region, prior to the electrodes being substantially affected by the presence of analyte. In certain electrochemical assays where the Debye layer is by the tear biomarker assay and is detected by a change is capacitance of the system, the baseline reading can be correlated to tear osmolarity, and the dynamic change in capacitance over time can indicate the levels of tear biomarker. Thus, the osmolarity and biomarker output signals are produced from the same electrodes but are separated in time, the osmolarity output occurring substantially immediately upon introduction of the sample fluid to the sample region and the biomarker output occurring after a diffusion time for the sample region.

Other embodiments allow for the osmolarity to be determined at a different frequency spectrum than the biomarker assay. For example, the osmolarity can be determined by a 10-100 kHz impedance spectra, and the tear biomarker concentration analyzed by a DC or low frequency amperometric or voltammetric steady state measurement. Alternatively, the osmolarity can be determined by a 10-100 kHz impedance spectra, and the tear biomarker concentration analyzed by a 100 kHz-GHz excited nanostructure spectra, or THz adsorption spectra. Other combinations of pulsed, or sinusoidal electrochemical measurements, including the addition of a small sinusoidal signal atop a square wave input, can be used for such analyses.

Other aspects in accordance with the invention can include analysis of tear osmolarity and tear biomarkers to be analyzed in parallel nanofluidic chambers, and then normalized against each other.

Still other aspects of the invention include for the implementation where two separate tear samples are taken and analyzed in serial. Serial analyses of tear biomarker and tear osmolarity would give an indirect estimate the impact of sampling. It is likely that sequential analysis, if performed properly, would give a better indication of the tear homeostasis than unnormalized biomarker analysis alone.

While certain embodiments have been described above, it will be understood that the embodiments described are by way of example only. Accordingly, the inventions should not be limited based on the described embodiments. Rather, the scope of the inventions described herein should only be limited in light of the claims that follow when taken in conjunction with the above description and accompanying drawings.

What is claimed is:

1. A fluid measuring system for measuring osmolarity of a sample fluid and concentration of a biomarker within the sample fluid, said system comprising:
   a. a sample chip configured to contain an aliquot volume of a sample fluid, and which processes (i) energy properties of the sample fluid to prepare an osmolarity output signal which corresponds to osmolarity of the sample fluid, and (ii) chemical properties of the sample fluid to prepare a biomarker output signal which corresponds to concentration of a biomarker within the sample fluid; and
   b. a processing device that: receives the osmolarity output signal from the sample region and processes the osmolarity output signal to produce an osmolarity value for the sample fluid; and receives the biomarker output signal from the sample region and processes the biomarker output signal to produce a biomarker concentration value for the sample fluid;
   wherein the biomarker is: IgE, IgA, IgG, IgM, glucose, insulin, lactoferrin, a cytokine, a hormone, a hormone metabolite, an infectious disease phenotype, a nucleic acid, a protein, or a lipid fraction.

2. The fluid measuring system of claim 1, further comprising normalization of biomarker concentration values.

3. The fluid measuring system of claim 2, wherein the normalization of biomarker concentration values corrects for patient-specific tear homeostasis.

4. The fluid measuring system of claim 2, wherein the normalization of biomarker concentration values corrects for clinician induced tear sampling variance in connection with obtaining the sample fluid.

5. The fluid measuring system of claim 1, wherein the analyses of osmolarity and of the biomarkers are performed simultaneously.

6. The fluid measuring system of claim 1, wherein the analyses of osmolarity and of the biomarkers are performed serially.

7. The fluid measuring system of claim 2, wherein the normalization of biomarker concentration values is linear.

8. The fluid measuring system of claim 2, wherein the normalization of biomarker concentration values is ratiometric.

9. The fluid measuring system of claim 2, wherein the normalization of biomarker concentration values is exponential.

10. The fluid measuring system of claim 2, wherein the normalization of biomarker concentration values is based on a calibration curve.

11. The fluid measuring system of claim 1, wherein the sample region contains a plurality of electrodes.

12. The fluid measuring system of claim 11, wherein the plurality of electrodes are constructed from a non-polarizing metal.

13. The fluid measuring system of claim 11, wherein the plurality of electrodes are coupled to a conductive polymer.

14. The fluid measuring system of claim 11, wherein the plurality of electrodes are coupled to an electrochemical transducer.

15. The fluid measuring system of claim 1, wherein the sample region contains an optical transducer.

16. The fluid measuring system of claim 1, wherein the osmolarity and biomarker output signals are multiplexed in space.

17. The fluid measuring system of claim 1, wherein the osmolarity and biomarker output signals are multiplexed in time.

18. The fluid measuring system of claim 1, wherein the osmolarity and biomarker output signals are multiplexed in frequency.

19. The fluid measuring system of claim 1, wherein the osmolarity and biomarker output signals are multiplexed in transduction mechanism.

20. The fluid measuring system of claim 2, wherein the normalization of biomarker concentration values is multiplicative.

21. A method of measuring osmolarity of a sample fluid and concentration of a biomarker within the sample fluid, the method comprising:
   a. receiving from a sample region of a sample chip an osmolarity output signal that corresponds to osmolarity of the sample fluid, and a biomarker output signal that corresponds to concentration of a biomarker within the sample fluid, wherein the biomarker is selected from: IgE, IgA, IgG, IgM, glucose, insulin, lactoferrin, a cytokine, a hormone, a hormone metabolite, an infectious disease phenotype, a nucleic acid, a protein, or a lipid fraction; and
   b. processing the osmolarity output signal to produce an osmolarity value for the sample fluid and the biomarker output signal to produce a biomarker concentration value for the sample fluid.

22. The method of claim 21, further comprising determining an Adjusted Biomarker Level that provides normalization of biomarker concentration values.

23. The method of claim 22, wherein normalization of biomarker concentration values corrects for patient-specific tear homeostasis.

24. The method of claim 22, wherein normalization of biomarker concentration values corrects for clinician induced tear sampling variance in connection with obtaining the sample fluid.

25. The method of claim 21, wherein processing the osmolarity output signal and processing the biomarker output signal are performed simultaneously.

26. The method of claim 21, wherein processing the osmolarity output signal and processing the biomarker output signal are performed serially.

27. The method of claim 22, wherein normalization of biomarker concentration values is linear.

28. The method of claim 22, wherein normalization of biomarker concentration values is ratiometric.

29. The method of claim 22, wherein normalization of biomarker concentration values is exponential.

30. The method of claim 22, wherein normalization of biomarker concentration values is based on a calibration curve.

31. The method of claim 21, wherein the sample region contains a plurality of electrodes.

32. The method of claim 31, wherein the plurality of electrodes are constructed from a non-polarizing metal.

33. The method of claim 31, wherein the plurality of electrodes are coupled to a conductive polymer.

34. The method of claim 31, wherein the plurality of electrodes are coupled to an electrochemical transducer.

35. The method of claim 21, wherein the sample region contains an optical transducer.

36. The method of claim 21, wherein the output signals are multiplexed in space.

37. The method of claim 21, wherein the output signals are multiplexed in time.

38. The method of claim 21, wherein the output signals are multiplexed in frequency.

39. The method of claim 21, wherein the output signals are multiplexed in transduction mechanism.

* * * * *